(12) United States Patent
Shenfeld

(10) Patent No.: US 11,464,183 B2
(45) Date of Patent: Oct. 11, 2022

(54) NON-GM IMPROVED CROPS AND METHODS FOR OBTAINING CROPS WITH IMPROVED INHERITABLE TRAITS

(71) Applicant: Epigenetics Ltd, Rehovot (IL)

(72) Inventor: Avner Shenfeld, Rehovot (IL)

(73) Assignee: Epigenetics Ltd., Rehovot (IL)

( * ) Notice: Subject to any disclaimer, the term of this patent is extended or adjusted under 35 U.S.C. 154(b) by 0 days.

(21) Appl. No.: 15/965,060

(22) Filed: Apr. 27, 2018

(65) Prior Publication Data

US 2018/0242541 A1    Aug. 30, 2018

Related U.S. Application Data

(63) Continuation of application No. PCT/IL2016/051179, filed on Nov. 1, 2016.

(60) Provisional application No. 62/249,962, filed on Nov. 3, 2015, provisional application No. 62/264,868, filed on Dec. 9, 2015.

(51) Int. Cl.
*A01H 3/02* (2006.01)

(52) U.S. Cl.
CPC ..................................... *A01H 3/02* (2013.01)

(58) Field of Classification Search
None
See application file for complete search history.

(56) References Cited

U.S. PATENT DOCUMENTS

| | | | | |
|---|---|---|---|---|
| 8,901,369 B2 * | 12/2014 | De Block | ............... | A01H 3/00 800/260 |
| 8,935,880 B2 | 1/2015 | Ovadya et al. | | |
| 2012/0117678 A1 | 5/2012 | De Block | | |
| 2013/0117877 A1 | 5/2013 | Akpo et al. | | |
| 2014/0259905 A1 | 9/2014 | Ovadya et al. | | |

OTHER PUBLICATIONS

Galloway and Etterson, Nov. 16, 2007; vol. 318, pp. 1134-1136.*
Springer, N., Trends in Genetics, Apr. 2013; vol. 29, No. 4, pp. 241-247.*
Hauben, M. et al. PNAS; Nov. 24, 2009; vol. 106, No. 47, pp. 20109-20114. (Year: 2009).*
International Search Report and Written Opinion from International Application No. PCT/IL201 6/051179 dated Jan. 24, 2017.
Dorais, "The use of supplemental lighting for vegetable crop production: light intensity, crop response, nutrition, crop management, cultural pratives", Canadian Greenhouse Confererence, Oct. 9, 2003, pp. 1-8.
Olle et al., "The effects of light-emitting diode lighting on greenhouse plant growth and quality", Agricultural and food science 22, No. 2, pp. 223-234, Jan. 1, 2013.
Ouzounis et al., "Predawn and high intensity application blue light decreases the quantum yield of PSII and enhances the amount of phenolic acids, and pigments in Lactuca sativa", Frontiers in plant science, 6, Feb. 26, 2015.
Hauben et al., "Energy use efficiency is characterized by an epigenetic component that can be directed through artificial selection to increase yield", PNAS, Nov. 24, 2009, vol. 106, No. 47, pp. 20109-20114.
Zhang et al., "Effects of shade and drought stress on soybean hormones and yield of main-stem and branch", African Journal of Biotechnology vol. 10(65), p. 14392-14398, Oct. 24, 2011.
Golden Bantam Corn—Heirloom Seeds, Vegetable Seeds—Sustainable Seed—Sustainable Seed Company, retrieved Apr. 20, 2018 <<http://sustainableseedco.com/helrloom-vegetable-seeds/ce-k/corn-heirloomseeds/heirioom-sweet-cor-seed/original-8-row-golden-bantamcorn.html>>.
Corn: Open Pollinated & Heirloom; True Gold <<http://www.smartgardener.com/plants/218-corn-true-gold/overview>>.
Ben-Asher et al., "Effect of high temperature on photosynthesis and transpiration of sweet corn (*Zea mays* L. Var. Yugosa)", Photosynthetica 46 (4): 595-603, 2008.

* cited by examiner

*Primary Examiner* — Russell Kallis
(74) *Attorney, Agent, or Firm* — The Webb Law Firm

(57) ABSTRACT

The present invention discloses a non-GM method for producing a crop exhibiting improved traits compared to a control population of plants of the same crop species comprising the steps of providing a population of plants, exposing said population of plants to a predetermined light treatment regime by irradiating with artificial light in a specific wavelength range, monitoring at least one trait of said plants of step (b), comparing to said control population and selecting at least the top about 0.5%, preferably 1-2% plants having the best improved trait of said plants of previous step, propagating at least one subsequent generation of said at least 0.5%, preferably 1-2%, best improved trait plants, optionally repeating previous steps for least one subsequent generation, thereby obtaining a crop exhibiting an improved trait, wherein the improved trait is inheritable for at least one more generation, preferably for two or more generations, more preferably for 3 to 5 generations, and even more preferably for 6 to 8 generations.

6 Claims, 22 Drawing Sheets
(22 of 22 Drawing Sheet(s) Filed in Color)

Treated Soybean Plants

Bantam Line

True gold line

NON-GM IMPROVED CROPS AND METHODS FOR OBTAINING CROPS WITH IMPROVED INHERITABLE TRAITS

CROSS REFERENCE TO RELATED APPLICATIONS

This application is a continuation of International Application No. PCT/IL2016/051179, filed Nov. 1, 2016, which claims priority to U.S. Provisional Patent Application Ser. No. 62/249,962, filed on Nov. 3, 2015 and U.S. Provisional Patent Application Ser. No. 62/264,868 filed on Dec. 9, 2015, the entire contents of each of which are hereby incorporated by reference in their entirety.

FIELD OF THE INVENTION

The present invention discloses non-GM improved crops and methods for obtaining crops with improved inheritable traits.

BACKGROUND

Improvement of agricultural methods and productivity is seen as one of the greatest challenges of the $21^{st}$ century. According to the OECD-FAO report of 2012, agricultural production needs to be increased by 60% over the next 40 years, to meet the rising demand for food. Globally, the scope of area expansion is limited, i.e. the total arable land is projected to be increased by less than 5%. Thus, additional technologies will need to be developed in order to increase food production.

Traditionally, improved crops have been obtained by farmer experimentation with new varieties, plant breeding, purposeful selection, growth and cross-pollination.

The first genetically modified crop plant was produced in 1982. Genetically modified crops (GM or GMC) are plants whose DNA was modified using genetic engineering techniques with a view to introduce in the plants a non-natural trait.

Transgenic (GM) plants possess a particular trait not native to the plant, which trait is transmitted (inherited) through the seeds.

While the GM technology has been widely accepted in the US and other countries, the regulatory status of the GM foods varies by country, with some countries banning or restricting them, or permitting them within limiting regulations.

Up until now, the efforts to increase the intrinsic yield potential have mainly focused on exploiting the genetic variability within the crops. New combinations of plants have been mainly produced by traditional breeding techniques and molecular techniques, allowing the exchange of genetic material across species.

The role of epigenetic control mechanisms was much less studied and utilized. Epigenetics refers to the study of changes in gene expression or cellular phenotype, caused by mechanisms other than changes in the underlying DNA sequence.

Epigenetic mechanisms include functionally relevant modifications to the genome that do not involve a change in the nucleotide sequence. Examples of such modifications include DNA methylation and histone modification, both of which serve to regulate gene expression without altering the underlying DNA sequence. In such mechanisms, "non-genetic" factors cause the organism's genes to be expressed differently.

The role of epigenetic control components in plants was demonstrated in some studies and patent documents. US patent application 2013/0117877 A1 relates to methods of finding a DNA methylation profile for a plant with high energy use efficiency. The invention enables the artisan to correlate the DNA methylation profile of a plant with potentially high energy use efficiency. US patent application 2012/0117678 A1 as well as Hauben et al (2009) publication, disclose methods for selecting plants with high energy use efficiency, by monitoring their cellular respiration rate. The cellular respiration rate is determined by measuring NADPH content, ascorbic acid content and/or respiratory chain complex I activity. It is emphasized that the cellular respiration rate measurements taught by US patent application 2012/0117678 A1 and Hauben et al (2009), are performed in vitro, on explants or tissue samples isolated from individual plants. Furthermore, the prior art remains silent on the ability to induce the production of plants with high yield properties.

Attempts at manipulating the yield of plants and identifying yield genes have been made, with an emphasis on the modification of the flowering time in plants (U.S. Pat. No. 8,935,880 and U.S. Patent Application No. 2014/0259905).

There is an unmet and long felt need for non-GM improved crops and moreover, for non-GM crops with inheritable improved traits.

SUMMARY

This invention provides non-GM improved crops and methods for obtaining crops with improved inheritable traits.

It is an object of the present invention to provide a method for producing commercial plant crops (exemplified here by soybean, tomato, stevia and corn) exhibiting improved traits as compared to a control population of the same crop species, said method comprising the steps of: (a) providing a population of commercial crop plants; (b) exposing the population of commercial crop plants to a predetermined light treatment regime; and (c) monitoring at least one trait characteristic of the commercial crop plants of step (b) and comparing to the control population; wherein the method additionally comprises steps of: (d) irradiating with artificial light the plants of step (a) with light of wavelength in the range of about 380 nm to about 750 nm for a period of between about 5 minutes to about 2.5 hours, in the presence of ambient daylight characterized by luminous flux units of between about 1.5 to about 3000 lux; (e) identifying at least the top about 0.5%, preferably 1-2%, best performing plants of the plants of steps (b) and (c) as compared to the control population; (f) optionally, propagating at least one subsequent generation of the at least 0.5%, preferably 1-2%, best performing plants; and (g) optionally reiterating steps (b) to (f) on the at least one subsequent generation; thereby obtaining a commercial crop plant exhibiting improved traits compared to a control population of same and (h) at the end of the growing cycle of a treated plant, the best performing plants based on the selected trials were selected for at least one additional round of treatment.

It is a further object of the present invention to provide the method as defined above, wherein steps (d) to (g) are applied to plants or plant parts selected from the group consisting of seeds, seedlings, tissue cultures, calluses, meristems, regenerable cells, protoplasts, potted seedlings, adult plants and any combination thereof.

It is a further object of the present invention to provide the method as defined in any of the above, additionally comprising steps of selecting the control population from the group consisting of: untreated plants, untreated plants of the same generation, treated plants of the same generation and any combination thereof.

It is a further object of the present invention to disclose the method as defined in any of the above, wherein the ambient daylight is characterized by luminous flux units between about 100 to about 2000 lux.

It is a further object of the present invention to provide the method as defined in any of the above, wherein the step of irradiating with artificial light is applied at a periodicity selected from the group consisting of: at the beginning of sunrise, during dawn, during sunrise, during sunset or at any combination thereof.

It is a further object of the present invention to provide the method as defined in any of the above additionally comprising steps of irradiating with artificial light the plants of step (a) with red light wavelengths, particularly in the range of about 600 nm to about 700 nm.

It is a further object of the present invention to provide the method as defined in any of the above additionally comprising steps of irradiating with artificial light the plants of step (a) with wavelengths selected from the group consisting of red light, blue light, white light and any combination thereof.

It is a further object of the present invention to provide the method as defined in any of the above additionally comprising steps of irradiating with artificial light the plants of step (a) with red light wavelengths, blue light wavelengths, white light wavelengths and any combination thereof, consecutively, simultaneously or interchangeably.

It is a further object of the present invention to provide the method as defined in any of the above additionally comprising steps of irradiating with artificial light the plants of step (a) for a period of between about 5 minutes to about 2.5 hours, in the presence of ambient daylight, during dawn, every day for duration of up to 6 weeks from sowing.

It is a further object of the present invention to provide the method as defined in any of the above additionally comprising steps of exposing the crop plants to a predetermined light treatment regime for about one month under greenhouse conditions and then transferring the top plants responding to the treatment to field growth conditions. At the end of the growing cycle, the best performing plants, based on the selected traits are chosen for an additional round of treatment.

It is a further object of the present invention to provide the method as defined in any of the above additionally comprising steps of exposing the plants to a predetermined light treatment regime for about one month under field conditions and then selecting the plants responding best to the treatment. At the end of the growing cycle, the best performing plants, based on the selected traits are chosen for an additional round of treatment.

It is a further object of the present invention to disclose the method as defined in any of the above additionally comprising steps of monitoring at least one trait or parameter selected from the group consisting of: average seed number, fruit number, average seed weight, average single seed weight, plant height, main stem width, stem thickening, fruit weight, plant biomass, number of stems, number of secondary stems, photosynthesis efficiency, photosynthesis rate, nitrogen concentration in leaves and any combination thereof.

It is a further object of the present invention to provide the method as defined in any of the above additionally comprising steps of producing a commercial crop plant exhibiting an increased yield of at least 2% and up to 800 or more of the at least one yield characteristic, as compared to the control population of same.

It is a further object of the present invention to provide the method as defined in any of the above, wherein steps (d) to (g) are applied to plant species or plant types selected form the group consisting of Soybean, Maize, Rapeseed, Cotton, Corn, Wheat, Rice, Potato, Cassava, vegetables such as pepper and tomato, fruits, shrubs such as stevia, oil seed plant, herbs, flowering plants, medicinal plants, plants used for food, wood, wood products, fibers, drugs, oils, latex, pigments, clothing, fuels and resins industries, plants associated with any industrial use such as production of fine chemicals etc, and any combination thereof, additionally comprising steps of producing a commercial crop plant exhibiting improved traits such as an increased yield of between about 10% and about 200% of the at least one yield characteristic, as compared to the control population of same.

It is a further object of the present invention to provide the method as defined in any of the above additionally comprising steps of producing a commercial crop plant exhibiting an increased average seed number per plant of between about 10% and about 200%, preferably between about 50% and about 80%, as compared to the control population of same. The same method is applied to soybean.

It is a further object of the present invention to provide the method as defined in any of the above additionally comprising steps of producing a commercial crop plant exhibiting improved traits such as an increased average single seed weight of between about 10% and about 50%, preferably between about 20% and about 40% as compared to the control population of same.

It is a further object of the present invention to provide the method as defined in any of the above additionally comprising steps of producing a commercial crop plant exhibiting an improved trait such as an increased average total seed weight per plant of between about 50% and about 200%, preferably between about 80% and about 150% as compared to the control population of same.

It is a further object of the present invention to provide the methods of this invention wherein applied to a genetically modified (GM) or to a non-GM commercial crop plant.

It is a further object of the present invention to provide a plant part or a product thereof produced by the method as defined in any of the above.

It is a further object of the present invention to provide a commercial crop plant exhibiting improved traits such as increased yield compared to a control population of same, produced by the steps of: (a) providing a population of commercial crop plants; (b) exposing the population of commercial crop plants to a predetermined light treatment regime; (c) monitoring at least one yield characteristic of the commercial crop plants of step (b) and comparing to the control population; wherein the method additionally comprises steps of: (d) irradiating with artificial light the plants of step (a) with light of wavelength in the range of about 380 nm to about 750 nm for a period of between about 5 minutes to about 2.5 hours, in the presence of ambient daylight characterized by luminous flux units of between about 1.5 to about 3000 lux; (e) identifying at least the top about 0.5%, preferably 1-2%, highest yield plants of the plants of steps (b) and (c) as compared to the control population; (f) optionally, propagating at least one subsequent generation of the at least 0.5%, preferably 1-2%, highest yield plants; and (g) optionally reiterating steps (b) to (f) on the at least one subsequent generation; wherein the commercial crop plant preserves its increased yield capacity in at least one subsequent generation without exposure to an additional light treatment regime.

It is a further object of the present invention to provide a method for improving traits of commercial crops of genetically modified (GM) commercial crop plant or to a non GM commercial crop plant.

It is a further object of the present invention to provide a plant part or a product thereof derived from the commercial plant as defined in any of the above.

It is further within the scope of the invention to provide a method for manipulating the plant's genome expression to increase its energy production efficiency. This may result in a dramatic increase in the number of pods, seeds, fruits and biomass of the selected crop lines (e.g. soybean, tofu and oil among other crops). Using the methods of the present invention, it is demonstrated that a crop exhibiting increased yield capacity of up to 800% or more, between F1 (generation 1) and F3 (generation 3) or subsequent generation, can be produced.

It is a further object of the present invention to provide a plant or a harvestable part thereof produced by the method as defined in any of the above.

BRIEF DESCRIPTION OF THE FIGURES

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1:
Figure 2:
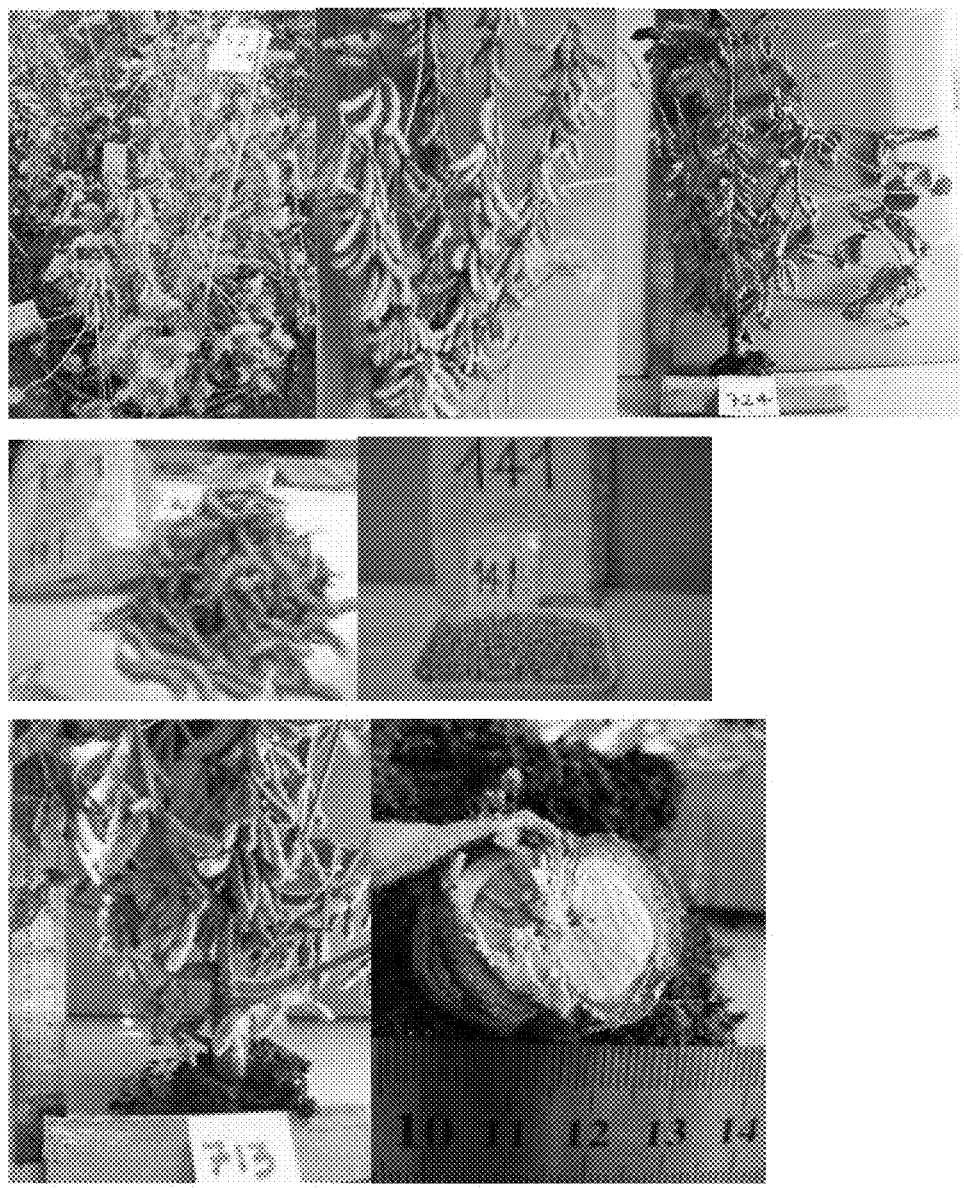
Figure 3:
Figure 4:
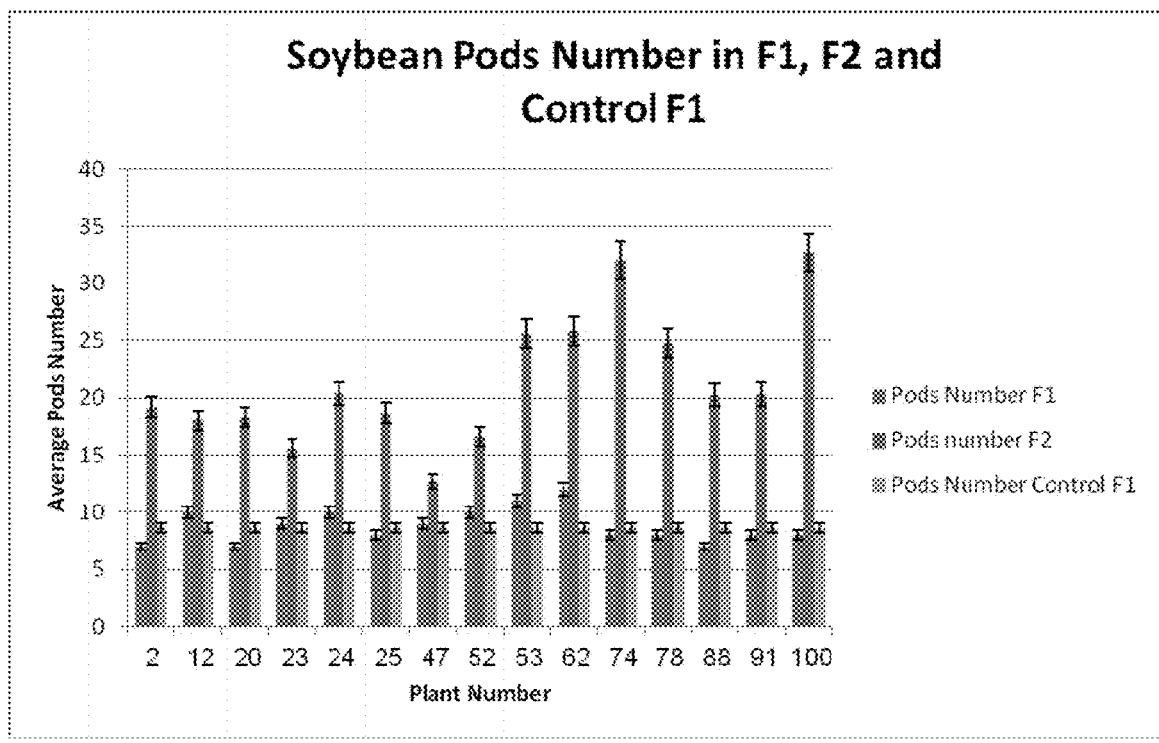
Figure 5:
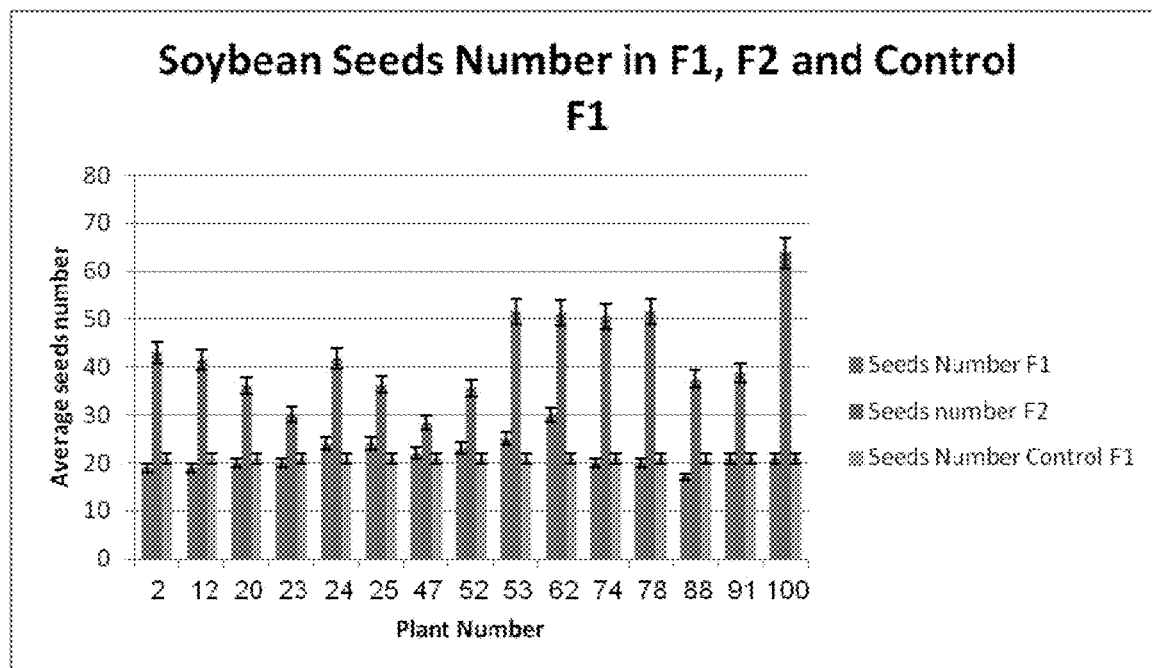
Figure 6:
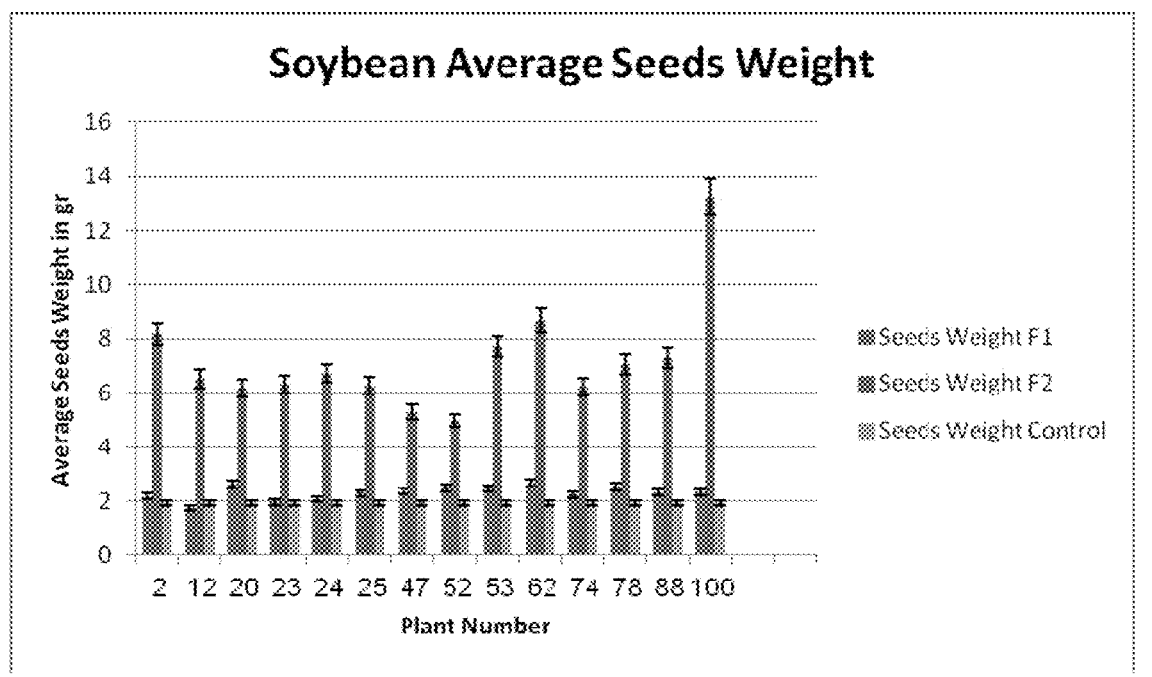
Figure 7:
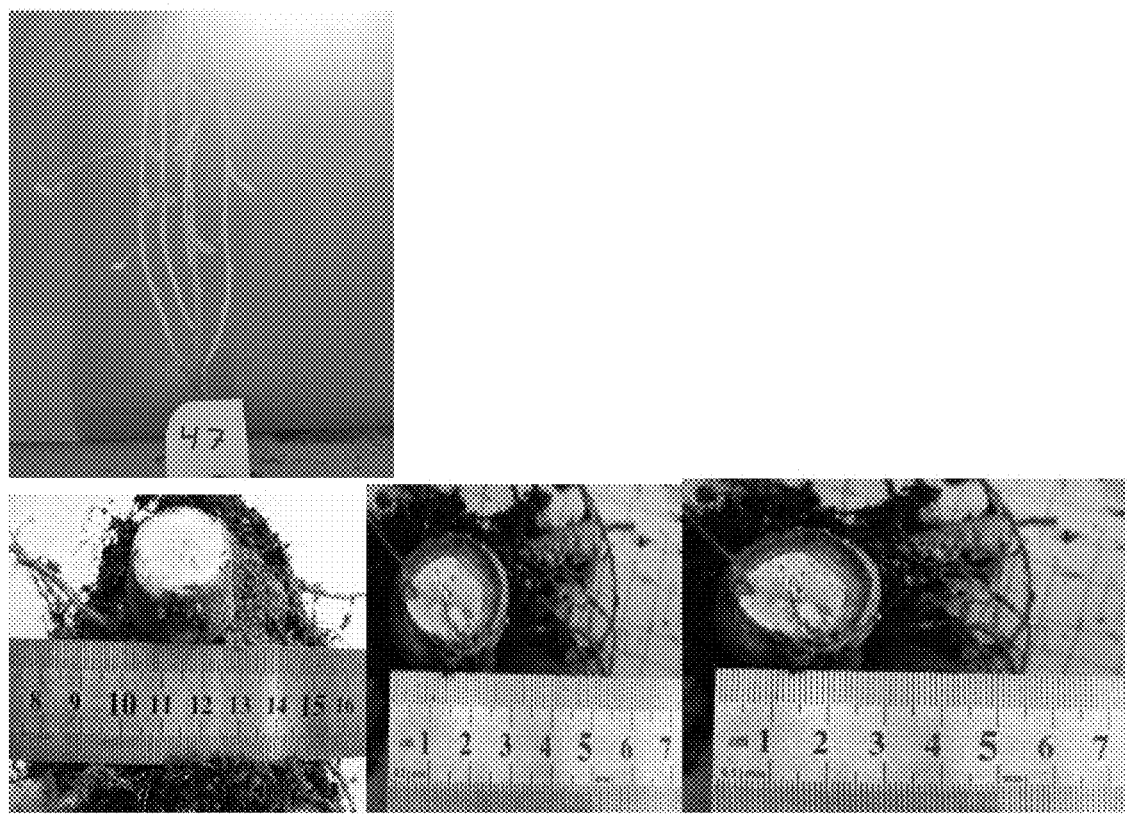
Figures 8, 9:
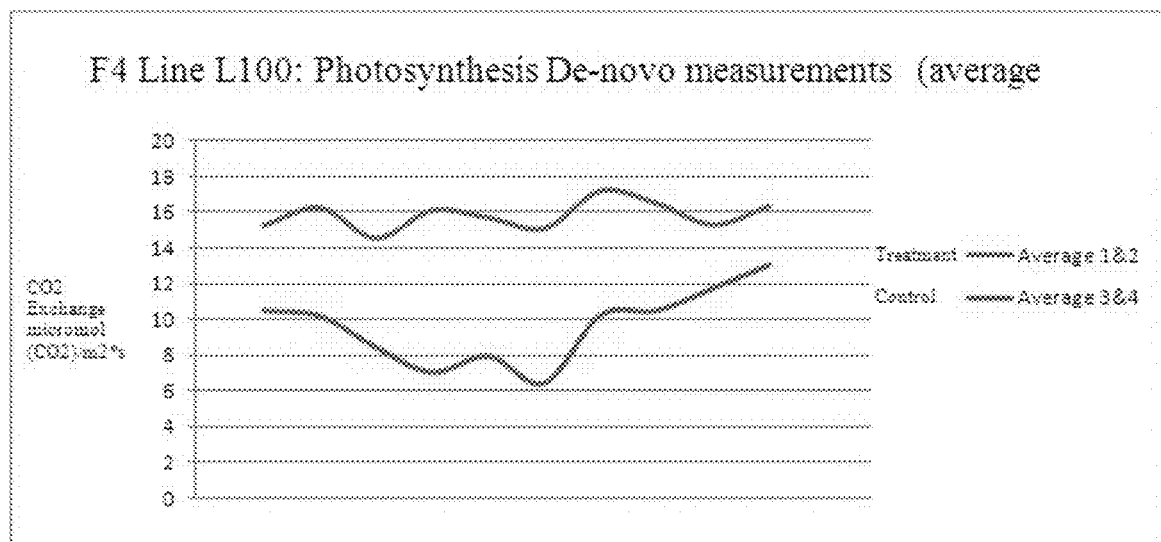

In order to better understand the invention and its implementation in practice, a plurality of embodiments will now be described, by way of non-limiting example only, with reference to the accompanying drawings, wherein FIG. 1 photographically presents a bush-like formation of F3 treated soybean plant (treated three times) with hundreds of pods;

FIG. 2 photographically presents selected F3 sub-lines treated with the red-light conditioning protocol of the present invention;

FIG. 3 photographically presents the F1 generation of treated plants versus plants generated from non-treated soybean plants at the age of 6 weeks;

FIG. 4 presents a graphic illustration of difference in soybean pods number between treated and none treated plants at F1 and F2 generations;

FIG. 5 presents a graphic illustration of difference in soybean seeds number between treated and none treated plants at F1 and F2 generations;

FIG. 6 presents a graphic illustration of average seeds weight of treated and none treated soybean plants at F1 and F2 generations;

FIG. 7 presents photographic illustrations of main stem of a control F1 soybean plant and treated F3 selected soybean plants;

FIG. 8 presents a graphic representation showing a comparison of photosynthesis level between treated and control soybean plants of F4 sub-line L-100; and control plants.

FIG. 9 presents a photographic representation of treated Stevia plants in comparison to control plants after 6 weeks.

Figure 10:
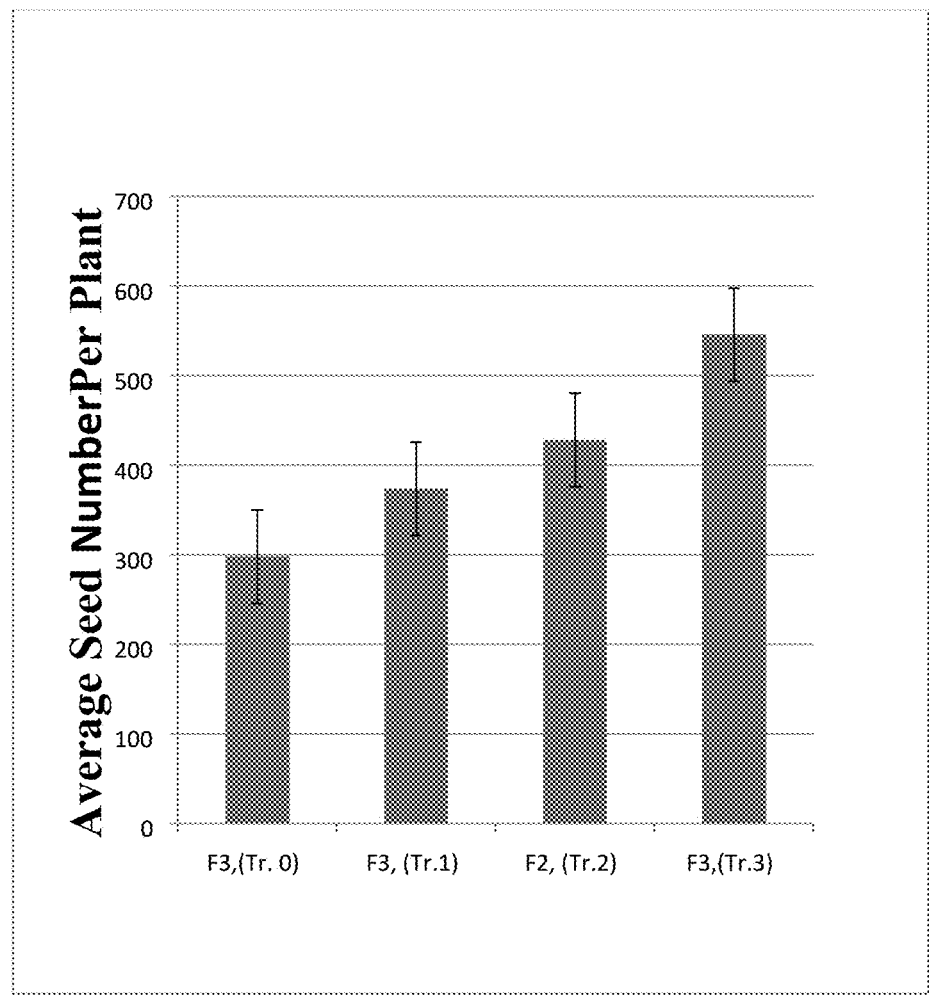

FIG. 10 is presenting a graphic illustration of the relative average seed number per plant in % of treated versus non treated Tofu line soybean seeds; (Tr. means one treatment, Tr.2 means two treatments).

Figure 11:
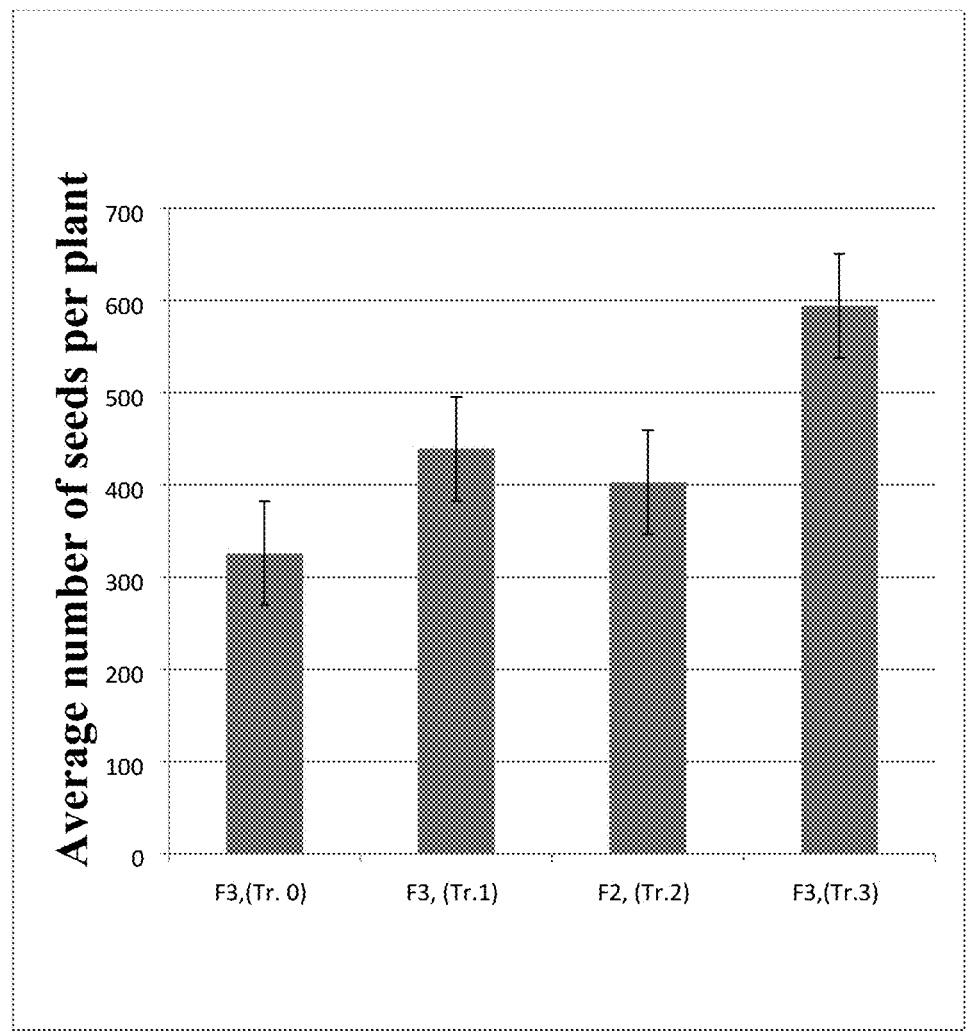
Figure 12:
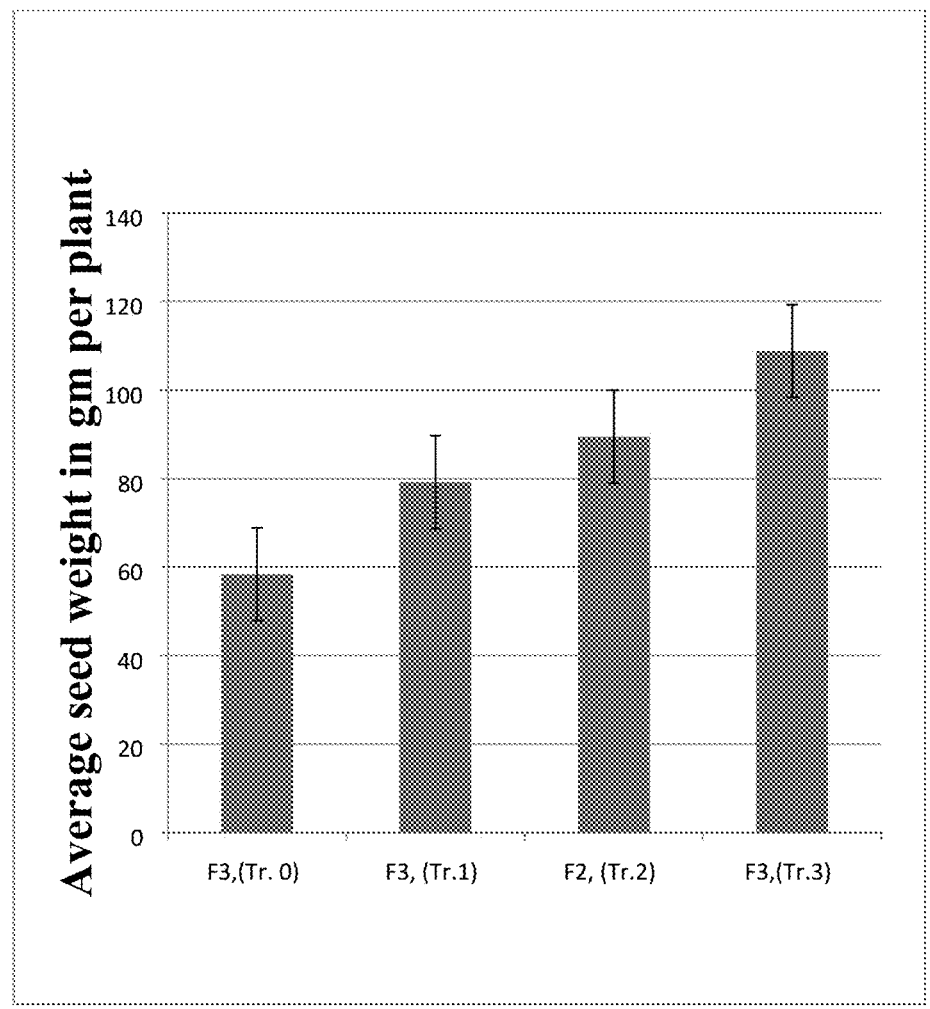
Figure 13:
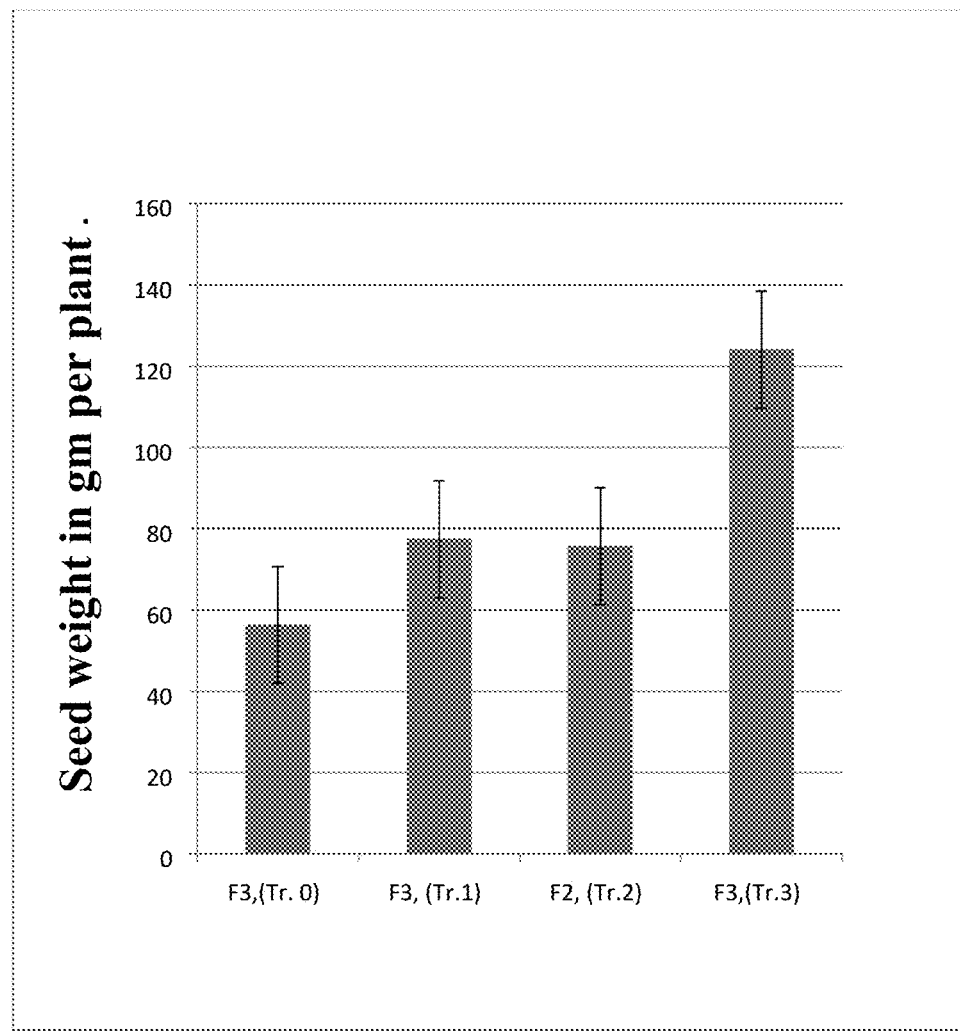
Figure 14:
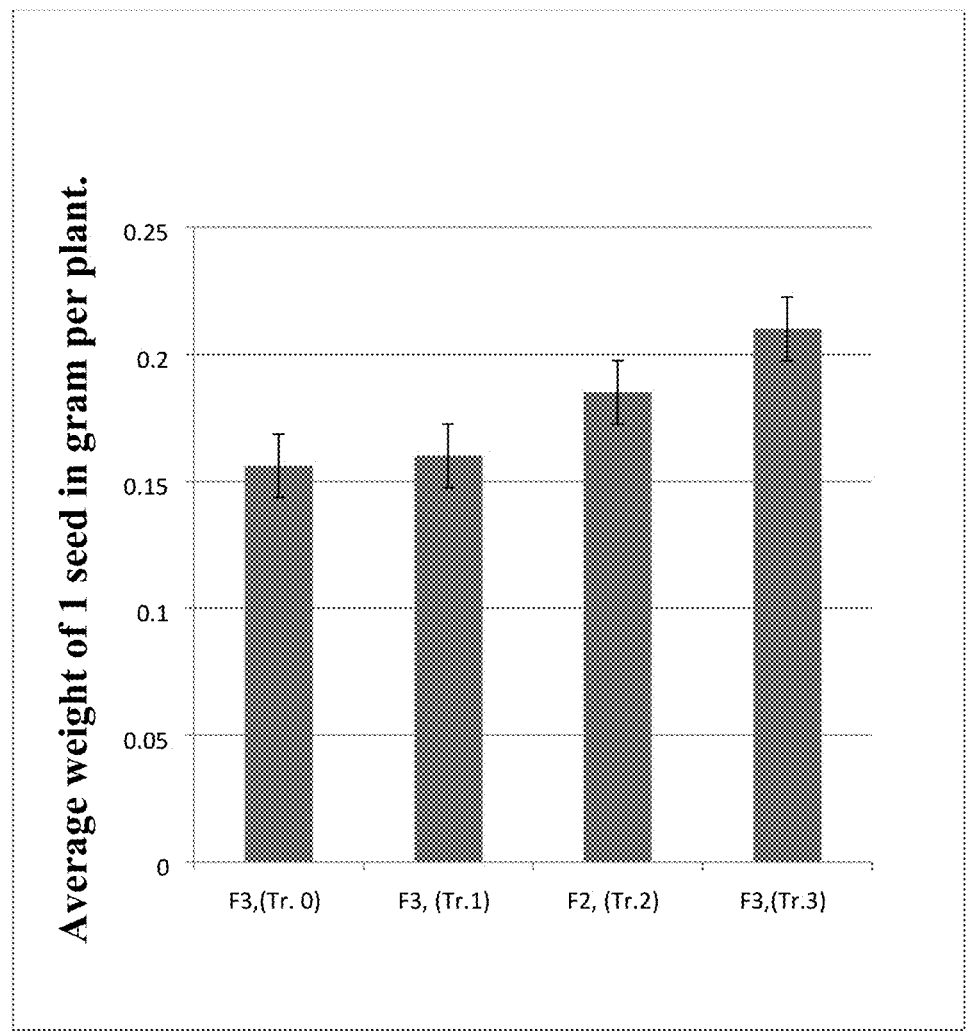
Figure 15:
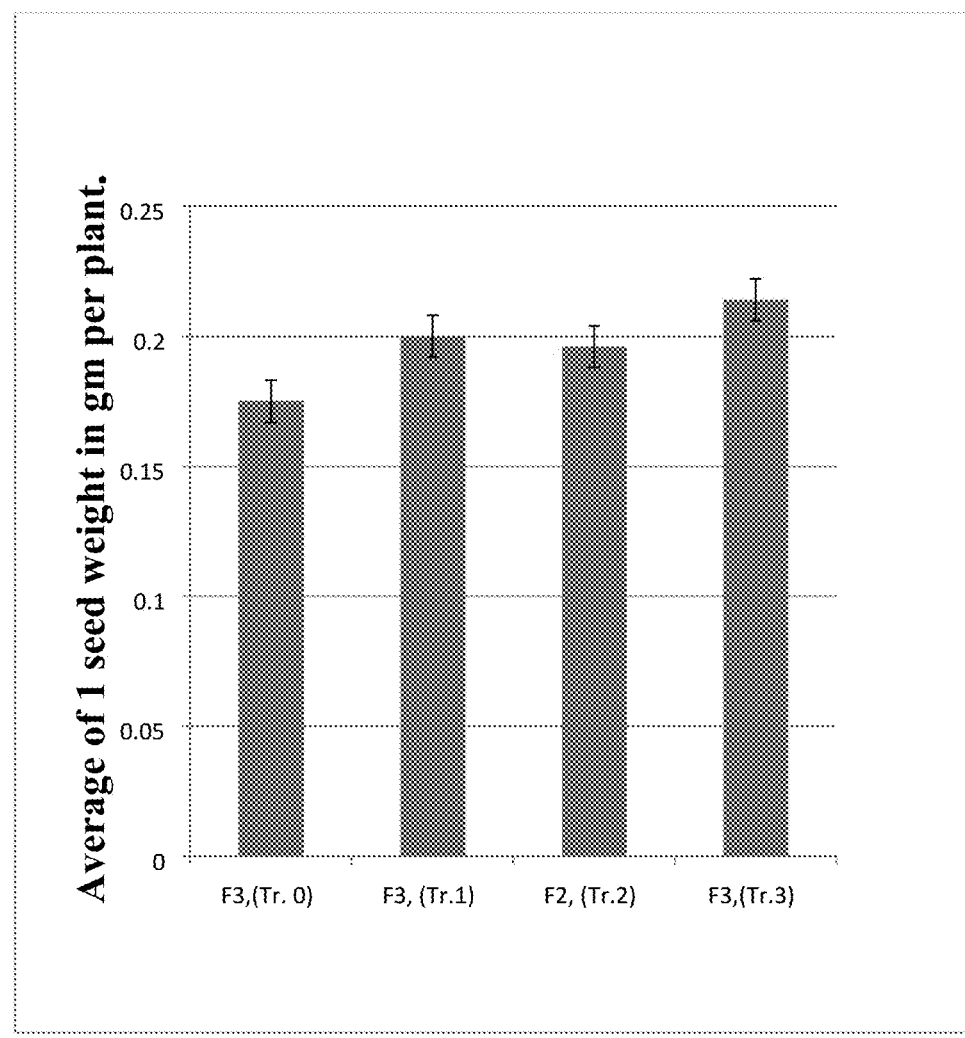
Figure 16:
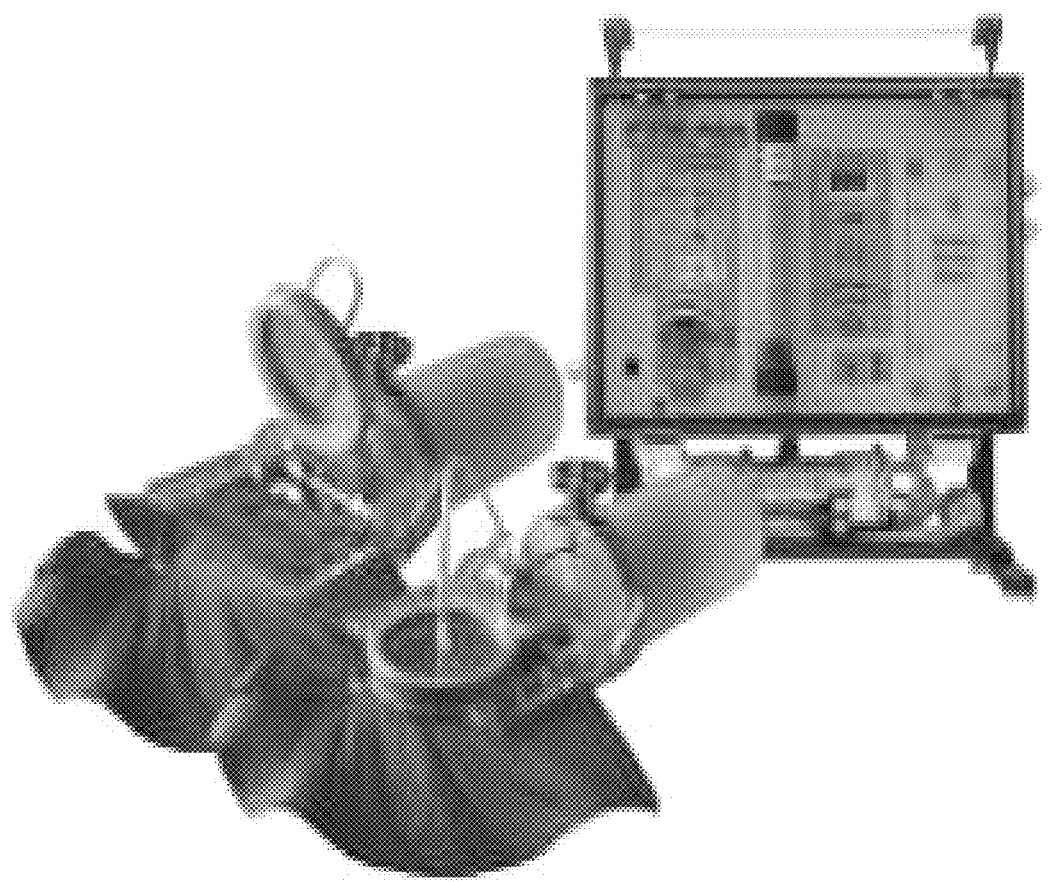
Figure 17:
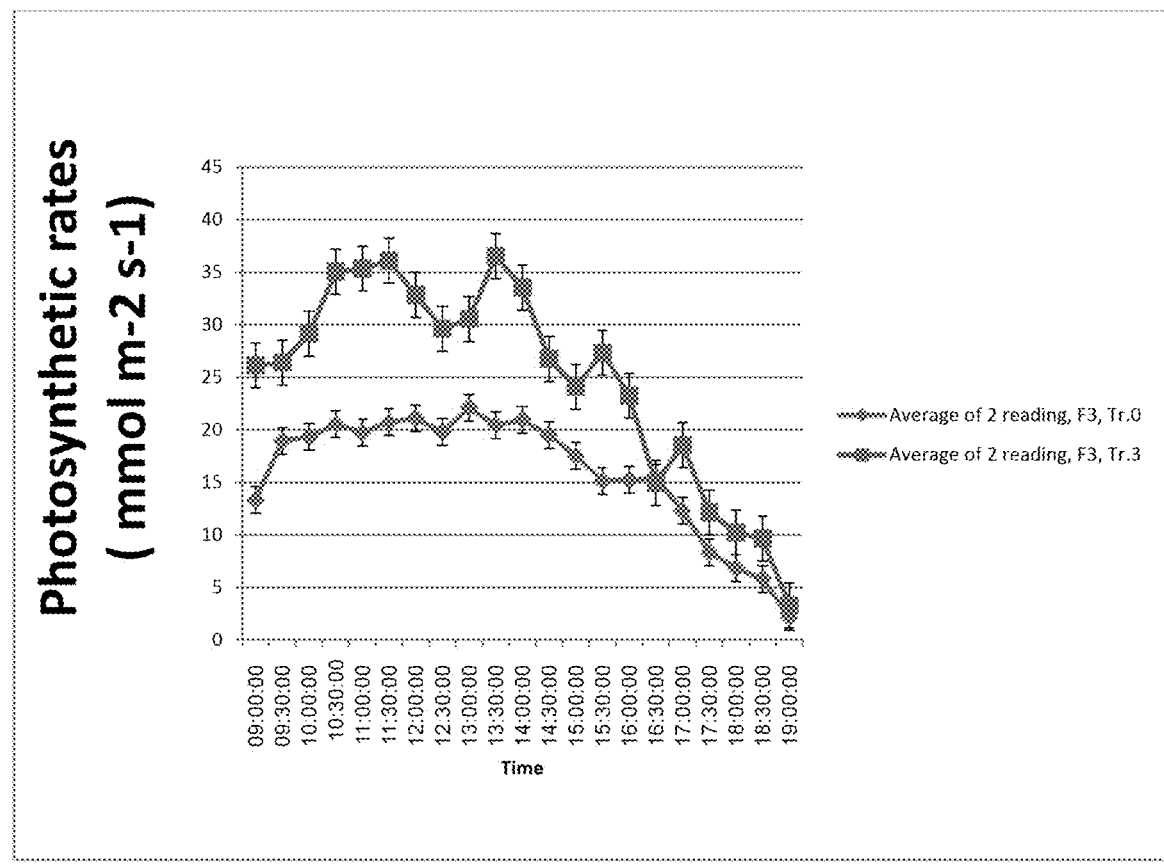
Figure 18:
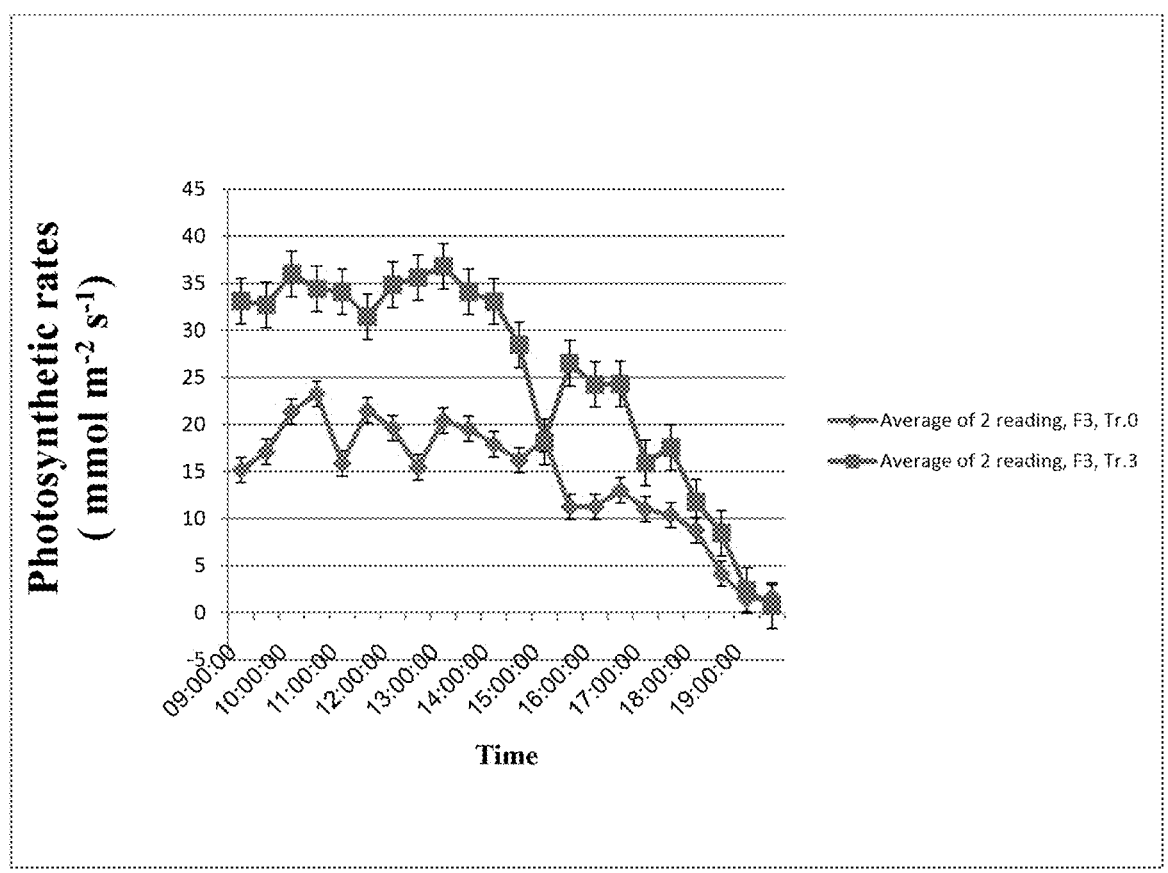
Figure 19:
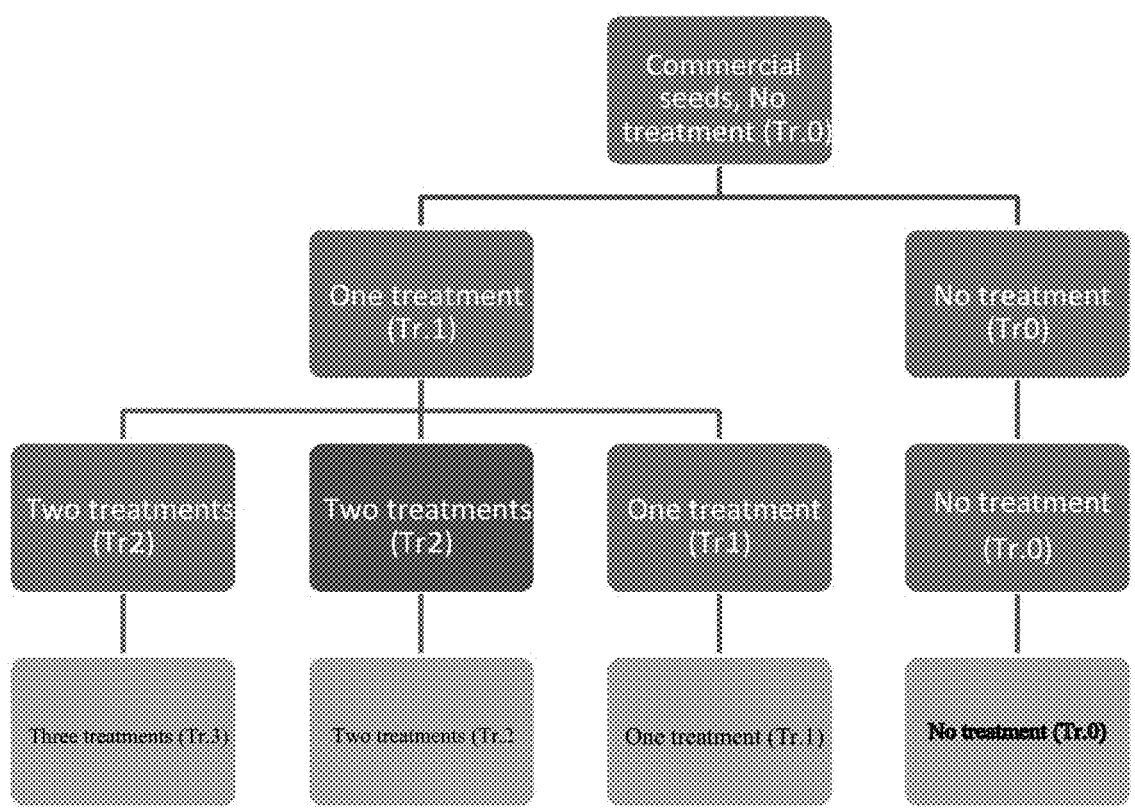
Figure 20:
Figure 21:
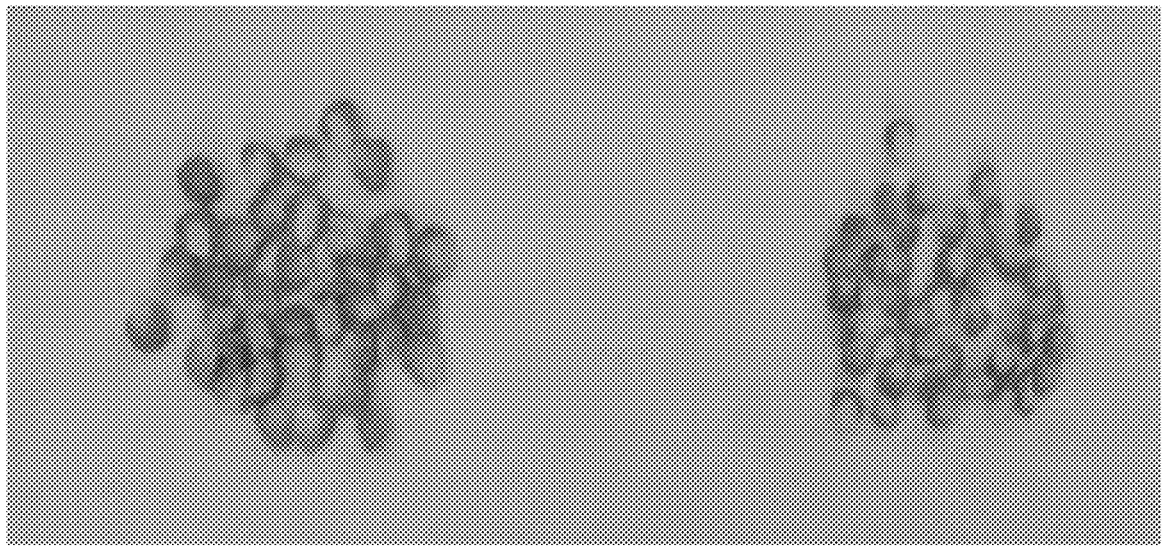

FIG. 11 is presenting a graphic illustration of the average seed number per plant of treated versus non treated oil soybean line seeds;

FIG. 12: is presenting a graphic illustration of the average seed weight (gr) of high yield sub-lines of treated versus non treated (Tr. 0) Tofu soybean line seeds;

FIG. 13: is presenting a graphic illustration of the average seed weight (gr) of high yield sub-lines of treated versus non treated (Tr. 0) oil soybean line seeds;

FIG. 14: is presenting a graphic illustration of the average weight of one seed (gr) of treated versus non treated (Tr. 0) Tofu soybean line seeds;

FIG. 15: is presenting a graphic illustration of the average weight of a single seed (gr) of treated versus non treated (Tr. 0) oil soybean line seeds;

FIG. 16: is presenting a photographic illustration of a photosynthesis and transpiration monitor PTM 48A (A) and an automatic self-clamping leaf chamber LC-4A (B), as embodiments of the present invention;

FIG. 17: is presenting a graphic illustration of the photosynthetic rate of treated (Tr.3) versus non treated (Tr.0) F3 'Bantam' line (corn) seeds;

FIG. 18: is presenting a graphic illustration of the photosynthetic rate of treated (Tr.3) versus non treated (Tr.0) F3 'True Gold' line seeds;

FIG. 19: is presenting a flow chart of seed generations and treatments applied to the seeds and/or seedlings in each generation, as an another embodiment of the present invention;

FIG. 20: presenting a photographic illustration of the multiple ears phenotype in (Tr. 3) F3 'Bantam' line; and FIG. 21: is presenting a photographic illustration of differences between the seeds of treated F3 plant (Tr. 3) and the control F3 (Tr. 0) in 'Bantam' line.

Figure 22:
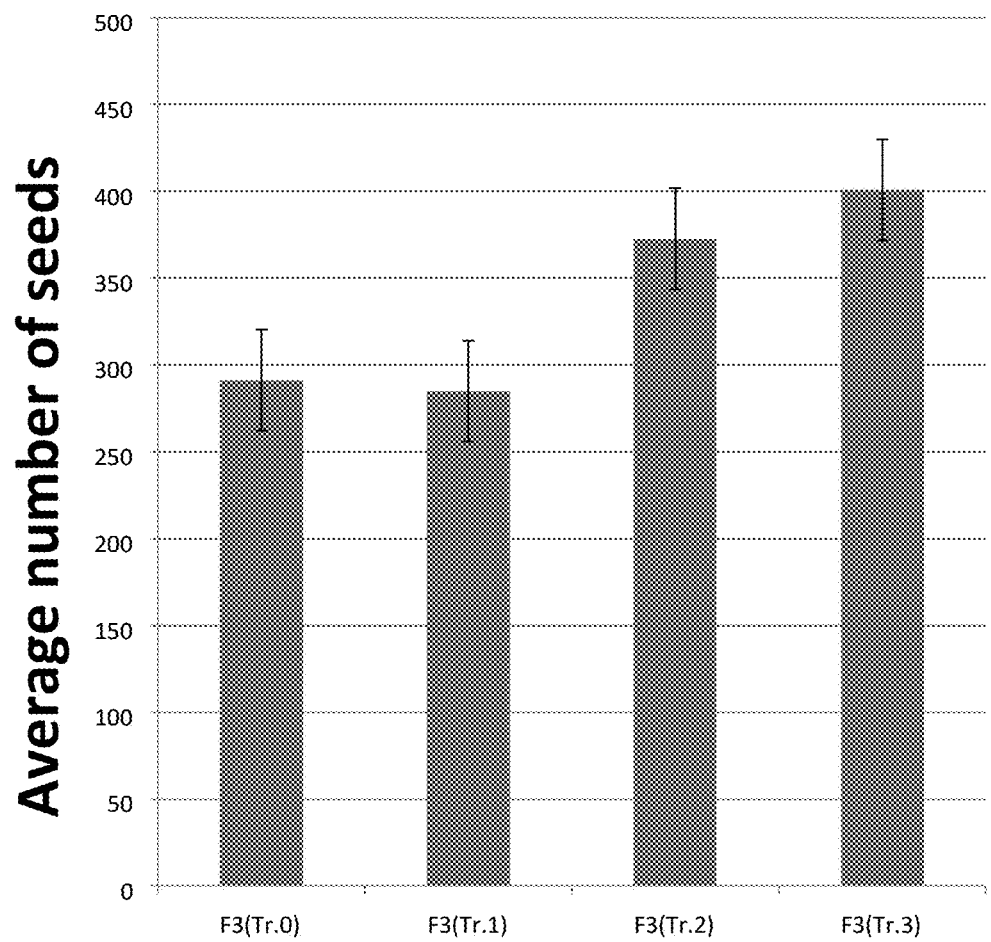

FIG. 22: is presenting the average number of seed per plant with corn Bantam line.

Figure 23:
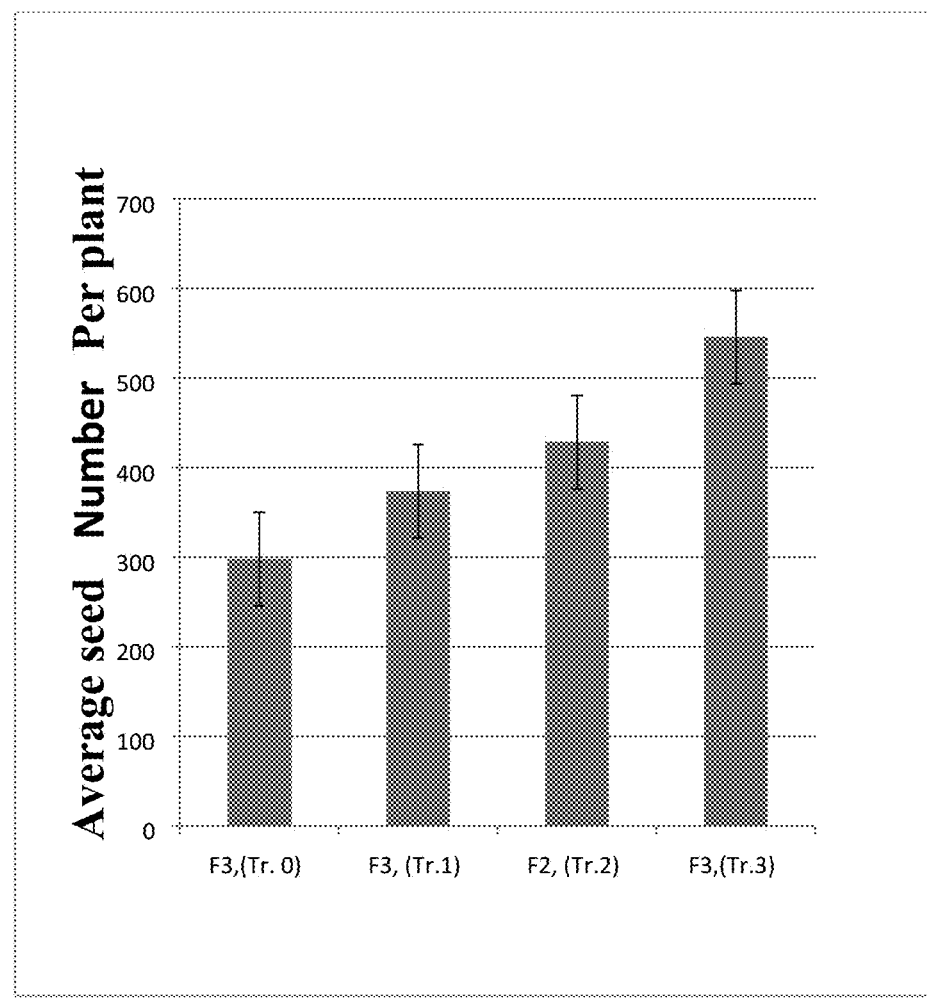

FIG. 23: is presenting the average number of seed per plant with corn True Gold line.

Figure 24:
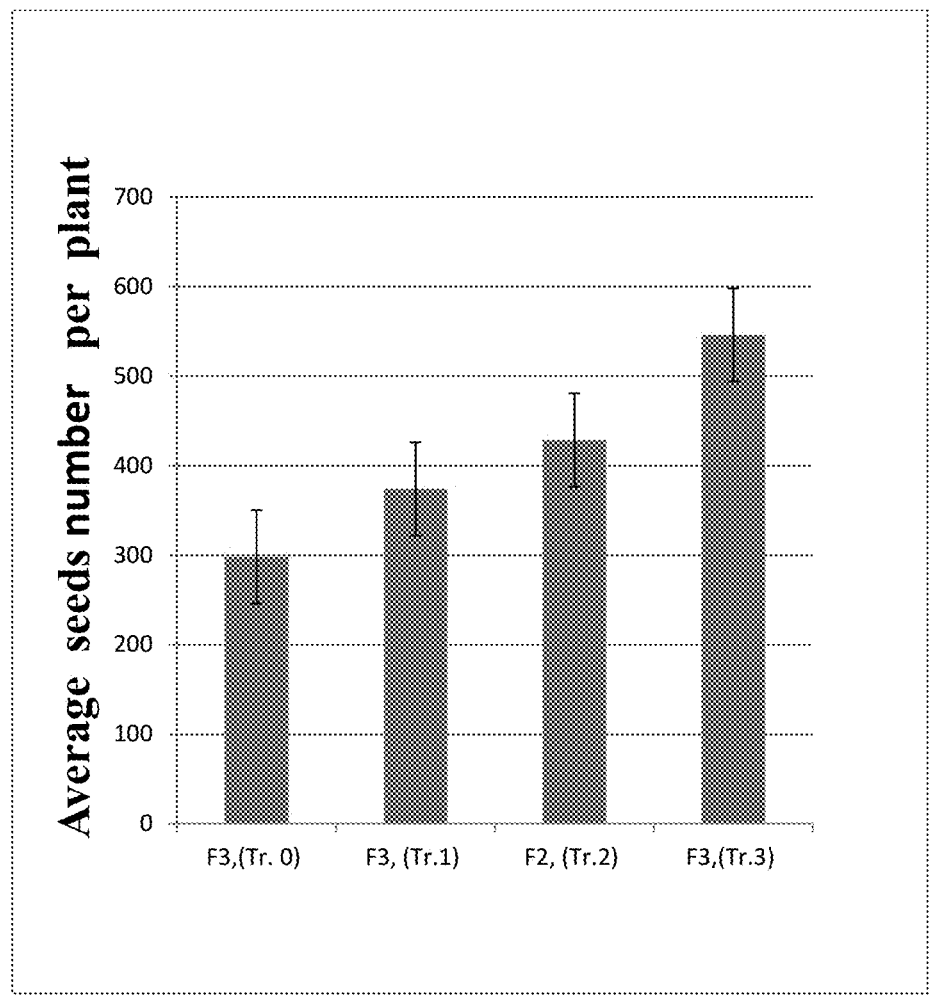

FIG. 24: is presenting a graphic illustration of the average seed number per plant of the treated vs. non treated Bantam line corn seeds.

Figure 25:
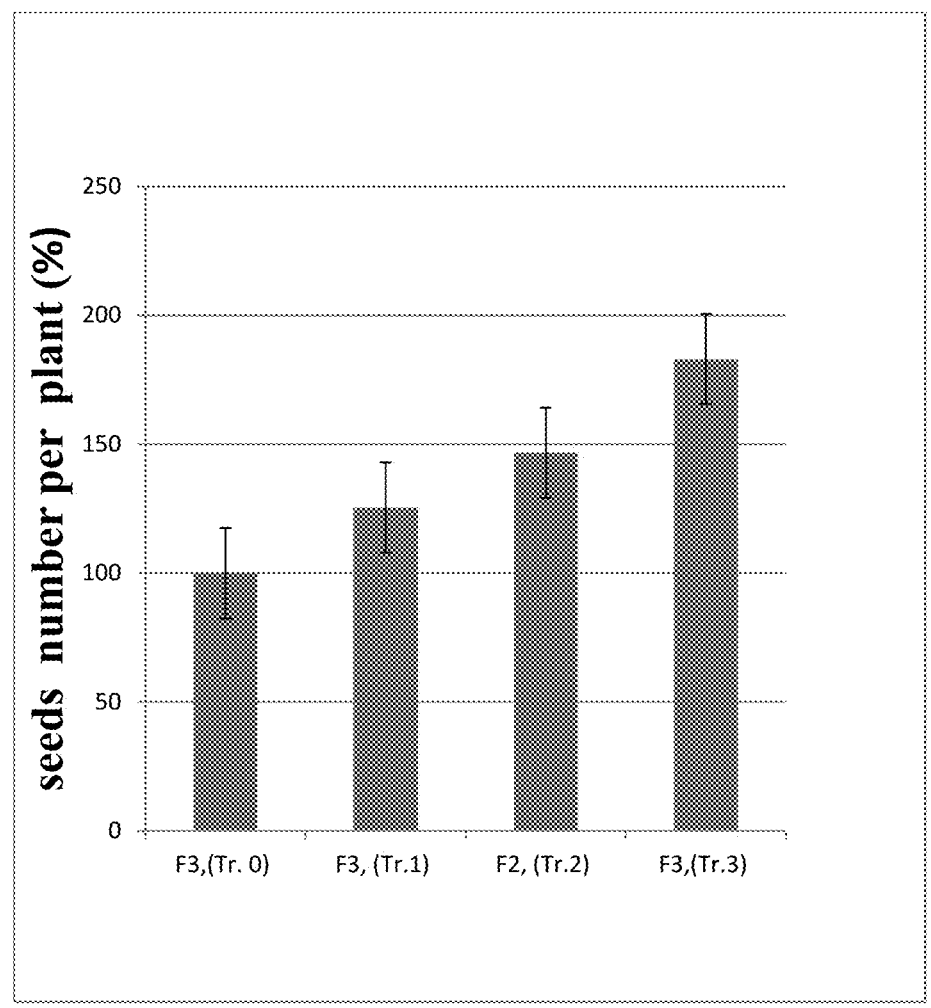

FIG. 25: is presenting a graphic illustration of the average number of seeds per plant of the treated vs. non treated True gold line corn seeds.

DETAILED DESCRIPTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide methods and products thereof for producing and screening for a commercial crop plant exhibiting increased yield compared to a control population of same.

In one embodiment the present invention provides a method for producing a commercial crop plant exhibiting improved traits (such as improved yield) compared to a control population of same. The method comprises the steps of: (a) providing a population of commercial crop plants; (b) exposing said population of commercial crop plants to a predetermined light treatment regime and (c) monitoring at least one yield characteristic of said commercial crop plants of step (b) and comparing to said control population.

Examples are provided where the crop plants are Soybean (Examples 1-4), Tomato (Example 5), Stevia (Example 6) and Corn crops (Examples 7-12).

It is within the scope that the aforementioned method additionally comprises steps of: (a) irradiating with artificial light with light of wavelength in the range of about 380 nm to about 750 nm for a period of between about 5 minutes to about 2.5 hours, in the presence of ambient daylight characterized by luminous flux units of between about 1.5 to about 3000 lux; (b) identifying at least the top about 0.5%, preferably 1-2%, highest yield plants of the plants identified above as compared to said control population; (c) optionally, propagating at least one subsequent generation of said at least 0.5%, preferably 1-2%, highest yield plants; and (d) optionally reiterating steps (b) to (f) on said at least one subsequent generation. In this way a commercial crop plant exhibiting improved traits compared to a control population of same is produced. It is further within the scope of the invention to disclose a method for improving plant traits by manipulating environmental factors affecting the plant's growth such as light radiation.

The technology provided by the present invention is suitable for genetically modified (GM) crops as well as to non-GM crops (i.e. produced by other techniques such as breeding, grafting etc.), but the method is non-GM and does not lead to GM modifications by itself.

It is further within the scope of the invention to provide various treatment protocols for affecting crop, preferably crop yield, resulting in different magnitude of trait improvements (such as yield increase, biomass increase, etc.) of the treated plants versus control plants.

In certain aspects, the treatment protocols are adjusted to the genomic structure of each crop. For example, at least two protocols were tested on soybean, resulting in different magnitude of yield increase of the treated plants versus control plants.

It is further within the scope of the invention to provide a method for manipulating the various plant traits by the method detailed in this invention.

According to certain aspects, the genomic or phenotypic changes are preserved in the next generations.

It is further demonstrated in the present invention that by increasing the efficiency of photosynthesis, crop lines characterized by improved traits such as high yield and better growth potential were produced and selected.

According to one embodiment, the present invention provides methods to increase the expression of genes which accelerate photosynthesis, by manipulating environmental factors. As a result, improved plant traits (such as an increase in plant growth, biomass increase, inheritable phenotypic changes) is achieved.

Without wishing to be bound by theory, the environmental effects on gene expression may be associated with epigenetic mechanisms. It is noted that such genes may be responsive to environmental influence. The improved traits acquired are inheritable over a number of generations (at least one more generation and up to 5-8 generations), without the need for GM.

According to a further embodiment, it is herein demonstrated that the ability to increase photosynthesis rate is associated with increased plant growth and with improved traits such as number of seeds per ear or plant, seed weight per ear or plant, average fruit number per plant, average seed number per plant, average seed weight per plant, plant height, main stem width, stem thickening, pods weight per plant, fruit weight per plant, average weight of a single seed, plant biomass, number of stems, number of secondary stems, stress resistance, pest resistance, virus resistance, drought tolerance, herbicide tolerance, delayed senescence, modified color, photosynthesis efficiency or rate, nitrogen concentration in the leaves, or any combination thereof.

According to a further embodiment, the improved trait plants of the present invention may be non-GM (Genetically Modified) or GM plants. It is noted that modifications in the treatment protocol of the present invention may be adapted to each crop type.

It is further within the scope that the treatment procedures (i.e. exposure to artificial environmental conditions) as well as the monitoring and evaluation of yield characteristics disclosed in the present invention are performed during the plant growth without disrupting the normal growth cycle of the plant. It is herein acknowledged that the treatment procedures are external, and in preferred embodiments, are directed to the whole plant. In any case, even when the treatment is done on seeds or plant parts, the treatment is non-invasive. Furthermore, the monitoring or selection or identification of high performing plants does not interrupt or interfere with plant growth.

It is further within the scope, that the invention can be applied to various crops and commercial lines including crops that are used for food consumption, for human and livestock industries, oil production, medicinal use, biodiesel, biomass increase and any other industrial use of the plants.

It is further to be understood that the phraseology and terminology employed herein is for the purpose of description and should not be regarded as limiting.

As used herein, the term 'about' refers to a value being ±25% of the defined measure.

The term "corn" as used herein also refers to maize. In certain aspects, a maize plant may be characterized by a leafy stalk producing ears which contain grains, which are seeds called kernels.

The term "commercial" or "commercial corn" or "commercial corn plant" as used herein refers to a cultivar or a line. In specific embodiments such cultivars or lines have been selected for characteristics such as improved yield, flavour, and resistance to disease. In further aspects they were produced by repeated self-fertilization or inbreeding.

The term "commercial" or "commercial crop" or "commercial crop plant" as used herein refers to a cultivar or a line. In specific embodiments such cultivars or lines have been selected for characteristics such as improved yield, flavour, and resistance to disease or environmental stress. In further aspects they were produced by repeated self-fertilization or inbreeding. The term "improved trait" as used herein refers to beneficial new traits acquired as a result of the treatment of the present invention by the treated plants as compared to untreated plants of the same.

The traits subject to improvement are selected from the group consisting of average fruit number per plant, average seed number per plant, average seed weight per plant, plant height, main stem width, stem thickening, pods weight per plant, fruit weight per plant, average weight of a single seed, plant biomass, number of stems, number of secondary stems, stress resistance, pest resistance, virus resistance, drought tolerance, herbicide tolerance, delayed senescence, modified color, photosynthesis efficiency or rate, nitrogen concentration in the leaves or any combination thereof.

The term "control population" as used herein refers to crop plants used as reference or in comparison to crop plants of the same species, variety, cultivar or commercial line that were exposed to the treatment of the present invention. Such control population may include untreated plants, untreated plants of the same generation, treated plants of the same generation and any combination thereof. In some embodiments yield parameters have been compared between treated crop plants and a control population.

According to further embodiments, the term 'control plant' or 'control population' as used in the context of the present invention refers to an untreated plant or a plant population of the same species or variety or line of the corresponding treated plant. In one aspect, the controlled plant did not receive additional light radiation treatment on top of normal (ambient) sunlight. In another aspect, 'control plant' or 'control population' used in the present invention refers to a corresponding plant of the same species or variety or line of the treated plant, exposed to the same number of treatment cycles as the treated plant, but propagated for one less generation than the treated plant. In another aspect, 'control plant' or 'control population' used in the present invention refers to a corresponding plant of the same species or variety or line of the treated plant, and of the same generation of the treated plant, exposed to less treatment cycles.

The term 'monocrop population' as used herein refers to a population composed of genetically singular crop plants. In other aspects, a monocrop population refers to crop plants of the same species or variety, particularly to the cultivation of a single crop species.

The term 'conditioning' as used herein refers to the application of at least one treatment regime or protocol as defined herein below, to a predetermined crop type, preferably corn, to achieve improved yield characteristics or parameters.

The term 'artificial light' as used herein refers to any lighting that is not sunlight. In general, artificial light refers to lighting with man-made sources, such as fluorescent, tungsten, mercury vapor, sodium vapor, halogen, compact fluorescent, etc. It can be turned on and off.

It is within the scope of the present invention that irradiation with artificial light includes exposing the plants to visible light wavelengths, corresponding to 380-750 nm and/or 450-495 nm. The following ranges can be used to distinguish between various light sources: violet (about 380-450 nm), blue (about 450-495 nm), green (about 495-570 nm), yellow (about 570-590 nm), orange (about 590-620 nm) and red (620-750 nm).

In specific embodiments, plants were exposed to irradiation with artificial light of wavelengths selected from red light, blue light, white light and any combination thereof, administered at predetermined protocols, periodicities, cycles and sessions.

The term 'ambient light' or 'ambient daylight' or 'ambient sunlight' as used herein refers to available or normal light or sources of light that are available naturally (e.g. the sun or moon). The term usually refers to the combination of all direct and indirect sunlight outdoors during the daytime. This includes direct sunlight, diffuse sky radiation that may be reflected from the Earth and terrestrial objects. It is within the scope of the invention that the outdoor illuminance can vary from 120,000 lux to less than 5 lux (even less than 1 lux for extreme cases). More specifically, the radiation treatment of the present invention is applied in the presence of ambient light characterized by luminous flux units of between about 1.5 to about 3000 lux, particularly between about 100 to about 2000 lux, more particularly in the range of about 800 lux to about 1800 lux.

The term 'dawn' as used herein generally refers to the time that marks the beginning of the twilight before sunrise. In other aspects, the term dawn, include sunrise, particularly a period of about one hour at the beginning of sunrise. The exact dawn time depends on day length.

The term 'sunset' as used herein generally refers to the time of sunset defined in astronomy as the moment when the trailing edge of the Sun's disk disappears below the horizon. The exact time of sunset depends on day length. In some aspects it may refer to a period of about 30 minutes to about 75 minutes before sunset.

The term "lux" as used herein refers to the measuring of luminous flux per unit area, i.e. one lux is equal to one lumen per square meter.

It is further within the scope of the present invention that the terms 'dawn' or 'sunrise' and 'sunset' are herein defined by light intensity or units of illuminance or luminous emittance or luminous flux per unit area of between about 1.5 to about 75 lux. It is noted that at sunset and sunrise (with a clear sky), ambient outdoor light may reach between about 400 lux and about 1800 lux.

The term 'treatment' as used herein refers to implementation of protocol comprising irradiation cycles with artificial light of wavelength ranges between 380 nm to about 750 nm, for duration of between 5 minutes to 2.5 hours per cycle. A predetermined session may be defined in terms of cycles, for example, there may be sessions of 5 minutes to 2.5 hours per day at a periodicity of 24 hours apart, for duration of 2 to 6 weeks. A treatment cycle is directed to one generation. According to certain aspects, the aforementioned irradiation treatment is applied in the presence of or in addition to normal or ambient daylight. The aforementioned treatment is applied to at least one crop plant or a crop plant part, preferably corn plant or corn plant part. In another aspect, the irradiation treatment is applied about one hour at the beginning of sunrise, during dawn or during sunset or a combination thereof (dependent on day length). It is noted that different combinations of light radiation treatments were applied to be suitable for the genomic structure and expression of each crop. Examples of treatment cycles used in the present invention may include the following:

In one embodiment, irradiation cycles comprising red light radiation wavelengths in the range of 600-700 nm or white light radiation or blue light wavelength or a combination thereof, were applied for a period of between 5 minutes to 2.5 hours, in the presence of ambient daylight, in the periodicity of about one hour at dawn, every day, for a session period of about one month from sowing into pots.

In an another embodiment, irradiation cycles comprising red light wavelengths in the range of 600-700 or white light or blue light or a combination thereof were applied for a period of about 60 min, in the periodicity of every day, during sunset, for a session period of about six weeks, from sowing the seeds into pots.

The term 'protocol A' as used herein refers to a treatment protocol where the crop plants or part thereof, were irradiated with white light, for one hour at dawn or during sunset, for about one month from the time of sowing. In specific embodiments, applying protocol A treatment resulted in a decreased yield or lower magnitude of yield increase of the treated crops relative to the control crops.

The term "protocol B" or 'treatment protocol' as used herein refers to a treatment protocol where the crops were irradiated with red light (wavelength in the range of 600-700 nm), for about one hour at dawn or during sunset, for about one month from the time of sowing. In specific embodiments, applying protocol B, the aforementioned treatment protocol resulted in an increased yield of the treated crops relative to the control crops.

As used herein, the term 'progeny' refers to the descendant(s) of a particular plant. Progeny may result from selfing (i.e., the same plant acts as the donor of both male and female gametes) or from crossing of two different plants. The descendant(s) can be, for example, of the F1, the F2, or any subsequent generation.

The terms 'increased yield' or 'high yield' as used herein refers to genetically or epigenetically enhanced lines or cultivars of crops such as soybean, corn, tomato, pepper etc. that have an increased crop production or increased percentage of usable plant parts, preferably fruits or seeds or biomass.

It is within the scope of the invention that the 'yield characteristic' or 'yield parameter' includes at least one phenotypic parameter or characteristic selected form the group comprising pods number per plant, average fruit number per plant, average seed number per plant, average seed weight per plant, plant height, main stem width, stem thickening, pods weight per plant, fruit weight per plant, average weight of a single seed, plant biomass, number of stems, number of secondary stems, photosynthesis efficiency or rate, nitrogen concentration in the leaves or any combination thereof.

The plants produced by the methods provided in this invention exhibit enhanced or improved or improved traits such as increased yield or improved measures of at least one of the parameters or characteristics listed above by at least 2% and up to 800% or more relative to a control plant. or control population.

As used herein, the term 'population' means a genetically homogeneous or heterogeneous collection of plants sharing a common genetic derivation.

As used herein, the term 'variety' or 'cultivar' means a group of similar plants that by structural features and performance can be identified from other varieties within the same species. The term 'variety' as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991.

The term 'plant cell culture' or 'tissue culture' as used herein means cultures of plant units such as, for example, protoplasts, regenerable cells, cell culture, cells, cells in plant tissues, pollen, pollen tubes, ovules, embryo sacs, zygotes and embryos at various stages of development, leaves, roots, root tips, anthers, meristematic cells, microspores, flowers, cotyledons, pistil, fruit, seeds, seed coat or any combination thereof.

The term 'plant material' or 'plant part' used herein refers to leaves, stems, roots, root tips, flowers or flower parts, seeds, fruits, pods, kernels, pollen, egg cells, zygotes, seed coat, cuttings, explant or any sample derived from a plant, cell or tissue cultures, or any other part or product derived from a plant or plant part and any combination thereof.

In other embodiments, the term 'plant material' or 'plant part' also refers to tissue culture of regenerable cells or protoplasts obtained from a plant or from a plant part selected from the group consisting of leaves, pollen, embryos, roots, root tips, anthers, flowers, fruit and seeds.

The term 'medicinal plants' as used herein generally refers to plants used in herbalism and thought to have medicinal properties. It is within the scope that such plants or their phytochemical constituents have been scientifically shown to have medicinal effects or have been approved by regulatory agencies such as the United States Food and Drug Administration or European Food Safety Authority. The American Society of Pharmacognosy defines medicines derived from natural sources, including plants and lists a category of medicinal plants.

The term 'industrial plants' or 'plants used for industry' generally refers to plant or plant parts used for applications vital to human such as foods (e.g., grains, seeds, fruits, and vegetables), wood and wood products, fibers, drugs, oils, fossil substances, latex, pigments, and resins, shelter, clothing, medicines, fuels, plants associated with any industrial use such as production of fine chemicals etc. and the raw materials from which innumerable other products are made.

The selection of the plants exhibiting the best improved traits is an important part of the methods of this invention.

Summing up, the method of this invention uses two selection stages that differ from each other:

1. The first selection takes place at the end of the irradiation period, when the plants best responding to the treatment are designated or selected and then transferred to field growth conditions.

2. The second selection takes place at the end of the growing period. This selection is based on the best preforming trait that was chosen (e.g. yield). The best preforming plants are selected for the next round of treatment. We have found that three rounds of treatment lead to the best heredity results.

Reference is now made to 1 photographically presenting a comparison between F3 treated soybean plant (treated three times) and a typical control soybean plant (published in the literature). As can be seen, the F3 treated soybean plants have significantly increased biomass relative to the untreated control soybean.

Reference is now made to FIG. 2 photographically presenting selected F3 sub-lines treated with the red-light conditioning protocol of the present invention. The exemplified F3 sub-lines include plant no. 141 of line 2B (2A) and plants no. 713 and 724 of line L88 (FIGS. 2B and 2C respectively).

Table 1 summarizes the improved yield characteristics of the selected F3 treated soybean sub-lines:

TABLE 1

Yield characteristics of selected F3 treated soybean sub-lines

| Line number | Plant number | Number of pods/ plant | Weight of pods gr/plant | Number of seeds/ plant | Weight of seeds gr/plant |
|---|---|---|---|---|---|
| 2B | 141 | 399 | 287.65 | 1069 | 183.20 |
| L88 | 724 | 201 | 150.61 | 515 | 106.18 |
| L88 | 713 | 197 | 132.07 | 530 | 89.13 |
| Control | 3166 | 43 | 11.63 | 93 | 7.85 |

According to certain aspects of the invention, the following conclusions are herein demonstrated: The treated plants of the present invention have a significantly increased average yield of up to several hundred percent (i.e. 700% or more) greater than the average yield of control plants, as exemplified above and in the Examples 1-4 for the soybean crops.

The treated plants preserve their high yield capacity from one generation to another without additional treatment for at least one generation.

The present invention provides at least two different treatment protocols. There is a difference between the two protocols of treatment on the effect on yield increase. One increases the yield while the other one decreases it or increases it in a lower magnitude.

The treated plants showed dramatic yield increase at F3 (i.e. exposed to Protocol B treatment) versus F2. Furthermore, only several lines reached a yield plateau at the second generation and exhibited similar yield capacity between the two generations, i.e. F2 and F3. It is herein acknowledged that in some lines, the yields increase beyond F3.

Plants that increase their yield as a result of the exposure to the herein provided treatment protocol, adjust their physiology to produce a large number of pods and/or seeds. For example, it is demonstrated that the main stem of the treated plants was reinforced and grew in width and structure. Moreover, the treated plants exhibited additional secondary stems and more biomass.

The increase in yield and growth of the treated plants appeared not only in the treated generation but continued to the next generation and was maintained without additional treatment. It is noted that the high yield plant may have adapted to the aforementioned major phenotypic changes, over time. The demand for energy is significantly higher in the high yield lines and the plants increase their energy supply to adjust to the new demands but the adaptation p method is continuous vertically through several generations.

Similarly, when exemplified for the corn crops (Examples 7-12), the following conclusions are herein demonstrated:

The treated plants of the present invention have a significantly increased average yield of up to several hundred percent (i.e. about 200% or more) greater than the average yield of control plants.

The treated plants preserve their high yield capacity from one generation to another without additional treatment for at least one generation.

The present invention provides at least one treatment protocols demonstrated to provide an effect on yield increase of corn.

The treated plants showed dramatic yield increase at F3 (i.e. F3, Tr.3) versus untreated F3 plants and versus F2 plants exposed to two treatments (F2, Tr. 2) and F3 plants exposed to one treatment (F3, Tr. 1). Furthermore, only several lines reached a yield plateau at the second generation and exhibited similar yield capacity between the two generations, i.e. F2 and F3. It is herein acknowledged that in some lines, the yields increases beyond F3.

Plants that increase their yield as a result of the exposure to the herein provided treatment protocol, may adjust their physiology to produce a large number of seeds. For example, the main stem of the treated plants may be reinforced and grow in width and structure. Moreover, the treated plants may exhibit additional secondary stems and more biomass.

The measured average photosynthetic rate of the treated plants (i.e. F3, Tr.3) is significantly higher than the measured average photosynthetic rate of the control plants (F3, Tr.0). Moreover, the peak photosynthetic rate value of the treated F3 line is about 80% higher than untreated F3 (Tr.0) at the same time point.

The increase in yield and growth of the treated plants appeared not only in the treated generation but continued to the next generation and was maintained without additional treatment. Without wishing to be bound by theory, it is noted that the demand for energy is significantly higher in the high yield lines and the plants increase their energy supply to adjust to the new demands, but the adaptation method is continuous vertically through several generations.

Thus, in one embodiment, the present invention provides a method for producing a corn plant, preferably commercial corn plant or line exhibiting increased yield capacity compared to a control population of plants of same comprising the steps of: (a) providing a population of commercial corn plants; (b) exposing the population of commercial corn plants to a predetermined light treatment regime; and (c) monitoring at least one yield characteristic of the commercial corn plants as defined above and comparing to the control population. According to further embodiments, the method as defined above additionally comprises steps of: (d) irradiating with artificial light the population of commercial corn plants with light of wavelength in the range of about 380 nm to about 750 nm for a period of between about 5 minutes to about 2.5 hours, in the presence of ambient daylight characterized by luminous flux units of between about 1.5 to about 3000 lux; (e) identifying at least the top about 0.5%, preferably 1-2%, highest yield plants of the plants exposed to a predetermined light treatment regime defined in any of the above, as compared to the control population; (f) optionally, propagating at least one subsequent generation of the at least 0.5%, preferably 1-2%, highest yield plants; and (g) optionally reiterating steps (b) to (f) on the at least one subsequent generation; thereby obtaining a commercial corn plant exhibiting increased yield compared to a control population of same.

According to a further embodiment, the method as defined in any of the above is applied to plants or plant parts selected from the group consisting of seeds, seedlings, tissue cultures, calluses, meristems, regenerable cells, protoplasts, potted seedlings, adult plants and any combination thereof.

According to a further embodiment, the method as defined in any of the above comprises additional steps of selecting the control population from the group consisting of: untreated plants, untreated plants of the same generation, treated plants of the same generation and any combination thereof.

It is further within the scope of this invention to provide the method as defined in any of the above, wherein the ambient daylight is characterized by luminous flux units between about 100 to about 2000 lux.

It is further within the scope to disclose the method as defined in any of the above, wherein the step of irradiating with artificial light is applied at a periodicity selected from the group consisting of: at the beginning of sunrise, during dawn, during sunrise, during sunset or at any combination thereof.

According to a further embodiment, the method as defined in any of the above additionally comprises steps of irradiating with artificial light the population of commercial corn plants as defined in any of the above with red light wavelengths, particularly in the range of about 600 nm to about 700 nm.

According to a further embodiment, the method as defined in any of the above additionally comprises steps of irradiating with artificial light the population of commercial corn plants as defined in any of the above with wavelengths selected from the group consisting of red light, blue light, white light and any combination thereof.

According to a further embodiment, the method as defined in any of the above additionally comprises steps of irradiating with artificial light the plants detailed above with a combination of red light wavelengths and white light wavelengths, consecutively, simultaneously or interchangeably.

According to a further embodiment, the method as defined in any of the above additionally comprises steps of irradiating with artificial light said plants population of step (a) with wavelengths selected from the group consisting of red light, blue light, white light and any combination thereof.

According to a further embodiment, the method commercial corn plants as defined in any of the above additionally comprises steps of irradiating with artificial light said plants of step (a) with red light wavelengths, blue light wavelengths, white light wavelengths and any combination thereof, consecutively, simultaneously or interchangeably.

According to a further embodiment, the method as defined in any of the above additionally comprises steps of irradiating with artificial light the population of commercial corn plants as defined in any of the above for a period of between about 5 minutes to about 2.5 hours, in the presence of ambient daylight, during dawn, every day for duration of 2 to 6 weeks from sowing.

According to a further embodiment, the method as defined in any of the above additionally comprises steps of irradiating with artificial light the population of commercial corn plants as defined in any of the above for a period of between about 5 minutes to about 2.5 hours in the presence of ambient daylight, during sunset, every day for duration of 2 to 6 weeks from sowing.

According to a further embodiment, the method as defined in any of the above additionally comprises steps of exposing the corn plants to a predetermined light treatment regime for about one month under greenhouse conditions and then transferring the top highest yield plants to field growth conditions.

According to a further aspect, the method as defined in any of the above additionally comprises steps of monitoring at least one parameter or characteristic selected from the group consisting of: average seed number, fruit number, average seed weight, average single seed weight, plant height, main stem width, stem thickening, fruit weight, plant biomass, number of stems, number of secondary stems, photosynthesis efficiency, photosynthesis rate, nitrogen concentration in leaves and any combination thereof.

According to a further embodiment, the method as defined in any of the above additionally comprises steps of producing a commercial corn plant exhibiting an increased yield of at least 2% and up to 800%, or more particularly 2%, 5%, 10%, 20%, 30%, 40%, 50%, 60%, 70%, 80%, 90%, 100%, 200%, 300%, 400%, 500%, 600%, 700%, 800%, 900% or more, of said at least one characteristic, as compared to the control population of same.

According to a further embodiment, the method as defined in any of the above, is applied to and is adapted to provide a yield increase effect on plant species or plant types selected form the group consisting of Soybean, Maize, Rapeseed, Cotton, Corn, Wheat, Rice, Potato, Cassava, vegetables such as pepper and tomato, fruits, shrubs such as stevia, oil seed plant, herbs, flowering plants, medicinal plants, plants used for food, wood, wood products, fibers, drugs, oils, latex, pigments, clothing, fuels and resins industries, plants associated with any industrial use such as production of fine chemicals etc and any combination thereof.

According to a further embodiment, the method as defined in any of the above additionally comprises steps of producing a commercial corn plant exhibiting an increased average seed number per plant of between about 10% and about 100%, preferably between about 50% and about 80%, as compared to the control population of same.

According to a further embodiment, the method as defined in any of the above additionally comprises steps of producing a commercial corn plant exhibiting an increased average single seed weight of between about 10% and about 50%, preferably between about 20% and about 40% as compared to the control population of same.

According to a further embodiment, the method as defined in any of the above additionally comprises steps of producing a commercial crop plant exhibiting an increased average total seed weight per plant of between about 50% and about 200%, preferably between about 80% and about 150% as compared to the control population of same.

It is further within the scope to disclose the method as defined in any of the above, wherein the method as defined in any of the above is applied to a genetically modified (GM) commercial crop plant or to a non GM commercial crop plant.

It is further within the scope to disclose a plant part or a product thereof produced by the method as defined in any of the above.

It is further within the scope of this invention to provide a commercial corn plant exhibiting an improved trait compared to a control population of same, produced by the steps of: (a) providing a population of commercial corn plants; (b) exposing the population of commercial corn plants to a predetermined light treatment regime; (c) monitoring at least one yield characteristic of the commercial corn plants as defined above and comparing to the control population.

It is further within the scope that the aforementioned method additionally comprises the steps of: (d) irradiating with artificial light the population of commercial corn plants as defined above with light of wavelength in the range of about 380 nm to about 750 nm for a period of between about 5 minutes to about 2.5 hours, in the presence of ambient daylight characterized by luminous flux units of between about 1.5 to about 3000 lux; (e) identifying at least the top about 0.5%, preferably 1-2%, highest yield plants of the plants exposed to a predetermined light treatment regime as compared to the control population; (f) optionally, propagating at least one subsequent generation of the at least 0.5%, preferably 1-2%, highest yield plants; and (g) optionally reiterating steps (b) to (f) on the at least one subsequent generation. It is further within the scope that the commercial corn plant preserves its increased yield capacity in at least one subsequent generation without exposure to an additional light treatment regime.

It is further within the scope to disclose the plant as defined in any of the above, wherein the steps as defined in any of the above are applied to plants or plant parts selected from the group consisting of seeds, seedlings, tissue cultures, calluses, meristems, regenerable cells, protoplasts, potted seedlings, adult plants and any combination thereof.

It is further within the scope to disclose the plant as defined in any of the above, wherein the control population is selected from the group consisting of: untreated plants, untreated plants of the same generation, treated plants of the same generation and any combination thereof.

It is further within the scope to disclose the plant as defined in any of the above, wherein the ambient daylight is characterized by luminous flux units between about 100 to about 2000 lux.

It is further within the scope to disclose the plant as defined in any of the above, wherein the step of irradiating with artificial light is applied at a periodicity selected from the group consisting of at the beginning of sunrise, during dawn, during sunrise, during sunset or at any combination thereof.

It is further within the scope to disclose the plant as defined in any of the above, further produced by steps of irradiating with artificial light the population of commercial corn plants as defined in any of the above, with red light wavelengths, particularly in the range of about 600 nm to about 700 nm.

It is further within the scope to disclose the plant as defined in any of the above further produced by steps of irradiating with artificial light the plants detailed above, with white light wavelengths.

According to a further aspect, the plant as defined in any of the above, further produced by steps of irradiating with artificial light the population of commercial corn plants detailed as defined in any of the above, with wavelengths in the red light wavelengths, blue light wavelengths, white light wavelengths and any combination thereof, It is further within the scope to disclose the plant as defined in any of the above, further produced by steps of irradiating with artificial light the population of commercial corn plants as defined in any of the above with red light wavelengths, blue light wavelengths, white light wavelengths and any combination thereof, in a consecutive, simultaneous or interchangeable manner. It is further within the scope to disclose a plant with improved traits produced by steps of irradiating with artificial light the population of commercial crop plants detailed in this disclosure, with a combination of red light wavelengths and blue light wavelengths, in a consecutive, simultaneous or interchangeable manner. According to a further aspect, the plant as defined in any of the above further produced by steps of irradiating with artificial light the plants detailed above for a period of between about 5 minutes to about 2.5 hours in the presence of ambient daylight, during dawn, every day for duration of 2 to 6 weeks from sowing.

It is further within the scope to disclose the plant as defined in any of the above, further produced by steps of irradiating with artificial light the population of commercial corn plants as defined in any of the above, for a period of between about 5 minutes to about 2.5 hours in the presence of ambient daylight, during sunset, every day for duration of 2 to 6 weeks from sowing.

It is further within the scope to disclose the plant as defined in any of the above further produced by steps of exposing the corn plants to a predetermined light treatment regime for about one month under greenhouse conditions and then transferring the top highest yield plants to field growth conditions.

It is further within the scope to disclose the plant as defined in any of the above, wherein the at least one characteristic is selected from the group consisting of: yield, average seed number, fruit number, average seeds weight, average single seed weight, plant height, main stem width, stem thickening, fruit weight, plant biomass, number of stems, number of secondary stems, photosynthesis efficiency, photosynthesis rate, nitrogen concentration in leaves and any combination thereof.

It is further within the scope to disclose the plant as defined in any of the above, wherein the plant exhibits an increased yield of between about at least 2% and about 800%, or more of the at least one yield characteristic, as compared to the control population of same.

It is further within the scope to disclose the plant as defined in any of the above wherein the plant exhibits an increased yield of between about 10% and about 200% of the at least one yield characteristic, as compared to the control population of same.

It is further within the scope to disclose the plant as defined in any of the above wherein the plant exhibits an increased average seed number per plant of between about 10% and about 100%, preferably between about 50% and about 80%, as compared the control population of same.

It is further within the scope to disclose the plant as defined in any of the above wherein the plant exhibits an increased average single seed weight of between about 10% and about 50%, preferably between about 20% and about 40% as compared to the control population of same.

It is further within the scope to disclose the plant as defined in any of the above wherein the plant exhibits an increased average total seed weight per plant of between about 50% and about 200%, preferably between about 80% and about 150% as compared to the control population of same.

It is further within the scope to disclose the plant as defined in any of the above, wherein the steps as defined in any of the above are applied to genetically modified (GM) commercial corn plant or to a non GM commercial corn plant.

It is further within the scope to disclose a plant part or a product thereof derived from the commercial corn plant as defined in any of the above.

It is further within the scope to provide a method of screening for plants exhibiting improved traits such as improved yield compared to a control population of same, the method comprises the steps of: (a) providing a population of commercial corn plants; (b) exposing the population of commercial crop plants to a predetermined light treatment regime; (c) monitoring at least one yield characteristic of the commercial crop plants of step (b) and comparing to the control population. The aforementioned method additionally comprises steps of: (d) irradiating with artificial light the population of commercial corn plants with light of wavelength in the range of about 380 nm to about 750 nm for a period of between about 5 minutes to about 2.5 hours, in the presence of ambient daylight characterized by luminous flux units of between about 1.5 to about 3000 lux; (e) identifying at least the top about 0.5%, preferably 1-2%, highest yield plants of the plants of steps (b) and (c) as compared to the control population; (f) optionally, propagating at least one subsequent generation of the at least 0.5%, preferably 1-2%, highest yield plants; and (g) optionally reiterating steps (b) to (f) on the at least one subsequent generation. In this way identifying a commercial corn plant exhibiting improved traits compared to a control population of same.

According to a further aspect, the method of screening for a commercial corn plant exhibiting increased yield compared to a control population of same as defined in any of the above additionally comprises steps of applying the steps as defined above to plants or plant parts selected from the group consisting of seeds, seedlings, tissue cultures, calluses, meristems, regenerable cells, protoplasts, potted seedlings, adult plants and any combination thereof.

It is further within the scope to disclose the method of screening for a commercial corn plant exhibiting increased yield compared to a control population of same as defined in any of the above, wherein the control population is selected from the group consisting of: untreated plants, untreated plants of the same generation, treated plants of the same generation and any combination thereof.

It is further within the scope to disclose the method of screening for a commercial corn plant exhibiting increased yield compared to a control population of same as defined in any of the above, wherein the ambient daylight is characterized by luminous flux units between about 100 to about 2000 lux.

It is further within the scope to disclose the method of screening for a commercial corn plant exhibiting increased yield compared to a control population of same as defined in any of the above, wherein the step of irradiating with artificial light is applied at a periodicity selected from the group consisting of: at the beginning of sunrise, during dawn, during sunrise, during sunset or at any combination thereof.

According to a further aspect, the method of screening for a commercial corn plant exhibiting increased yield compared to a control population of same as defined in any of the above additionally comprises steps of irradiating with artificial light the population of commercial plants with red light wavelengths, particularly in the range of about 600 nm to about 700 nm.

According to a further aspect, the method of screening for a commercial crop plant exhibiting increased yield compared to a control population of same as defined in any of the above additionally comprises steps of irradiating with artificial light the plants detailed above with white light wavelengths.

According to a further aspect, the method as defined in any of the above additionally comprises steps of irradiating with artificial light, population of commercial plants detailed above with wavelengths selected from the group consisting of red light, blue light, white light and any combination thereof.

According to a further embodiment, the method of screening for a commercial crop plant exhibiting increased yield compared to a control population of same as defined in any of the above additionally comprises steps of irradiating with artificial light the population of commercial plants with red light wavelengths, blue light wavelengths, white light wavelengths and any combination thereof, consecutively, simultaneously or interchangeably.

According to a further aspect, the method of screening for a commercial corn plant exhibiting increased yield compared to a control population of same as defined in any of the above additionally comprises steps of irradiating with artificial light the population of commercial plants detailed above with a combination of red light wavelengths and white light wavelengths, consecutively, simultaneously or interchangeably.

According to a further aspect, the method as defined in any of the above additionally comprises steps of irradiating with artificial light the plants detailed above for a period of between about 5 minutes to about 2.5 hours, in the presence of ambient daylight, during dawn, every day for duration of 2 to 6 weeks from sowing.

According to a further aspect, the method of screening for a commercial corn plant exhibiting increased yield compared to a control population of same as defined in any of the above additionally comprises steps of irradiating with artificial light the population of commercial plants for a period of between about 5 minutes to about 2.5 hours in the presence of ambient daylight, during sunset, every day for duration of 2 to 6 weeks from sowing.

According to a further aspect, the method of screening for a commercial corn plant exhibiting increased yield compared to a control population of same as defined in any of the above additionally comprises steps of exposing the corn plants to a predetermined light treatment regime for about one month under greenhouse conditions and then transferring the top highest yield plants to field growth conditions.

According to a further aspect, the method of screening for a commercial corn plant exhibiting increased yield compared to a control population of same as defined in any of the above additionally comprises steps of monitoring at least one yield parameter or characteristic selected from the group consisting of: average seed number, fruit number, average seed weight, average single seed weight, plant height, main stem width, stem thickening, fruit weight, plant biomass, number of stems, number of secondary stems, photosynthesis efficiency, photosynthesis rate, nitrogen concentration in leaves and any combination thereof.

According to a further aspect, the method of screening for a commercial corn plant exhibiting increased yield compared to a control population of same as defined in any of the above additionally comprises steps of producing a commercial corn plant exhibiting an increased yield of at least 2% and up to 800%, or more of the at least one yield characteristic, as compared to the control population of same.

According to a further aspect, the method as defined in any of the above wherein the steps detailed above are applied to and provide a yield increase effect on plant species or plant types selected form the group consisting of Soybean, Maize, Rapeseed, Cotton, Corn, Wheat, Rice, Potato, Cassava, vegetables such as pepper and tomato, fruits, shrubs such as stevia and oil seed plant, herbs, flowering plants, medicinal plants, plants used for food, wood, wood products, fibers, drugs, oils, latex, pigments, clothing, fuels and resins industries, any industrial use as production of fine chemicals etc, and any combination thereof.

According to a further aspect, the method of screening for a commercial corn plant exhibiting increased yield compared to a control population of same as defined in any of the above additionally comprises steps of producing a commercial corn plant exhibiting an increased average seed number per plant of between about 10% and about 100%, preferably between about 50% and about 80%, as compared to the control population of same.

According to a further aspect, the method of screening for a commercial corn plant exhibiting increased yield compared to a control population of same as defined in any of the above additionally comprises steps of producing a commercial corn plant exhibiting an increased average single seed weight of between about 10% and about 50%, preferably between about 20% and about 40% as compared to the control population of same.

According to a further aspect, the method of screening for a commercial corn plant exhibiting increased yield compared to a control population of same as defined in any of the above additionally comprises steps of producing a commercial corn plant exhibiting an increased average total seed weight per plant of between about 50% and about 200%, preferably between about 80% and about 150% as compared to the control population of same.

It is further within the scope to disclose the method of screening for a commercial corn plant exhibiting increased yield compared to a control population of same as defined in any of the above wherein the steps are applied to a genetically modified (GM) commercial corn plant or to a non GM commercial corn plant.

It is further within the scope to disclose a plant part or a product thereof produced by the method of screening for a commercial corn plant exhibiting increased yield compared to a control population of same as defined in any of the above.

In an embodiment, there is provided a non-GM method for producing a plant exhibiting improved traits compared to a control population or variety of plants of the same plant species comprising the steps of:
- (a) providing a population or variety of plants;
- (b) exposing said population or variety of plants to a predetermined light treatment regime by irradiating with artificial light in the presence of ambient daylight, characterized by luminous flux units of between about 1.5 to about 3000 lux, particularly from about 100 to about 2000 lux, every day for a duration of 2 to 6 weeks from sowing, wherein the predetermined light treatment regime of step (b) is selected from the group consisting of
  - (i) irradiating with artificial light of wavelength in the range of from about 380 nm to about 750 nm (visible range) for a period of from about 5 minutes to about 2.5 hours at selected times during the day,
  - (ii) irradiating with artificial light of wavelength in the range of from about 450 nm to about 490 nm (blue light) for a period of from about 30 minutes to about 2 hrs starting at sunrise,
  - (iii) irradiating with artificial light of wavelength in the range of from about 600 nm to about 700 nm (red light) for a period of from about 30 minutes, to about 60 minutes, starting about 30 min. before sunset, and optionally continuing about 30 minutes after sunset;
  - (iv) irradiating with artificial light of wavelength in the range of from about 450 nm to about 490 nm (blue light) for a period of about 30 minutes starting at sunrise followed by irradiation with artificial light of wavelength in the range of from about 600 nm to about 700 nm (red light) for a period of from about 30 minutes to about 60 minutes, starting 30 min. before sunset and optionally continuing about 30 minutes after sunset,
- or combinations thereof in a consecutive, simultaneous or interchangeable manner, optionally followed by the following steps:
  - (c) monitoring at least one trait of said plants of step (b) and comparing to said control population;
  - (d) selecting at least the top about 0.5%, preferably 1-2% plants having the best improved trait of said plants of step (b) and (c);
  - (e) propagating at least one subsequent generation of said at least 0.5%, preferably 1-2%, best improved trait plants; and
  - (f) optionally repeating steps (b) to (e) on said at least one subsequent generation;

thereby obtaining a crop exhibiting improved traits, wherein the improved traits are inheritable for at least one more generation, preferably for two or more generations, more preferably for 3 to 5 generations, and even more preferably for 6 to 8 generations.

The above predetermined light treatment (b)-(i)-(iv) of the population or variety of plants (a) leads to plants exhibiting improved traits. These plants and their harvestable parts may be used as such for producing improved crops.

The optional steps (c)-(f) may lead to further improvement of the monitored traits, as detailed in the Examples.

In another embodiment, there is provided a non-GM method for producing a plant exhibiting improved traits compared to a control population or variety of plants of the same plant species, wherein the improved inheritable trait being monitored is selected from the group consisting of yield, pods number, fruit number, seeds number, seeds weight, plant height, main stem width, stem thickening, pods weight, fruit weight, plant biomass, number of stems, number of secondary stems, stress resistance, pest resistance, virus resistance, drought tolerance, herbicide tolerance, delayed senescence, modified color, photosynthesis efficiency, nitrogen concentration in leaves and any combination thereof.

In one of the embodiments, the improved inheritable trait being monitored as detailed above is inheritable improved yield. The improved yield obtained by the method of this invention is at least 2% and up to 800%, or more particularly 2%, 5%, 10%, 20%, 30%, 40%, 50%, 60%, 70%, 80%, 90%, 100%, 200%, 300%, 400%, 500%, 600%, 700%, 800% or more, as compared to the control population of a control plant population of the same species.

In an embodiment, the inheritable improved trait in the plants treated with the method of this invention is the result of an epigenetic effect.

In another embodiment, the method of this invention is applied to plants or harvestable plant parts chosen from the group consisting of seeds, seedlings, tissue cultures, calluses, meristems, regenerable cells, protoplasts, potted seedlings, adult plants and any combination thereof.

In an embodiment, the irradiation step with artificial light in the method of this invention is applied at a periodicity selected from the group consisting of at the beginning of sunrise, during dawn, during sunrise, during sunset or at any combination thereof.

In another embodiment, the method of this invention is applied to plant species or plant types selected from the group consisting of Soybean, Maize, Rapeseed, Cotton, Corn, Wheat, Rice, Potato, Cassava, vegetables such as Pepper and Tomato, fruits, shrubs such as Stevia, oil seed plant, herbs, flowering plants, medicinal plants, plants used for food, wood, wood products, fibers, drugs, oils, latex, pigments, clothing, fuels and resins industries, plants associated with any industrial use such as production of fine chemicals etc, and any combination thereof.

In yet another embodiment, the method of this invention is applied to Soybean, Corn, Tomato or Stevia crops.

According to an embodiment, the method of this invention may be applied to a genetically modified (GM) plant or to a non-GM plant.

According to another embodiment, there is provided a plant or harvestable plant part with improved inheritable traits, wherein obtained by the method of this invention.

In an embodiment, there is provided a plant seed having an improved inheritable trait, wherein obtained by the method of this invention.

In another embodiment, there is provided a plant exhibiting an improved trait compared to a control population of plants of the same crop species wherein produced by the method of this invention wherein said plant preserves its improved trait for at least one subsequent generation, preferably for two or more generations, more preferably for 3 to 5 generations, and even more preferably for 6 to 8 generations, without exposure to additional light treatment.

According to an embodiment, there is provided a plant or harvestable plant part wherein produced by the method of this invention, applied to plants or harvestable plant parts chosen from the group consisting of seeds, seedlings, tissue cultures, calluses, meristems, regenerable cells, protoplasts, potted seedlings, adult plants and any combination thereof.

According to another embodiment, there is provided a plant or harvestable plant part wherein produced by the method of this invention, by irradiating a population of plants with artificial light in the red light wavelengths, blue light wavelengths, white light wavelengths and any combination thereof, in a consecutive, simultaneous or interchangeable manner.

In an embodiment, there is provided a plant or harvestable plant part with at least one improved inheritable trait in which said at least one improved inheritable trait is an yield characteristic selected from the group consisting of pods number, fruit number, seeds number, seeds weight, plant height, main stem width, stem thickening, pods weight, fruit weight, plant biomass, number of stems, number of secondary stems, photosynthesis efficiency, nitrogen concentration in leaves and any combination thereof. The plant or harvestable plant part exhibits as inheritable improved trait an increased yield of between about at least 2% and about 800%, or more, as compared to a control population of the same species.

In another embodiment, there is provided a plant or harvestable plant part produced by the method of this invention applied to plant species, harvestable plant part or plant types selected from the group consisting of Soybean, Maize, Rapeseed, Cotton, Corn, Wheat, Rice, Potato, Cassava, vegetables such as pepper and tomato, fruits, shrubs such as Stevia and oil seed plant, herbs, flowering plants, medicinal plants, plants used for food, wood, wood products, fibers, drugs, oils, latex, pigments, clothing, fuels and resins industries, plants associated with any industrial use such as production of fine chemicals etc and any combination thereof.

According to an embodiment, there is provided a plant or harvestable plant part produced by the method of this invention, applied to a genetically modified (GM) plant or to a non-GM plant.

According to another embodiment, there is provided a method of screening for plants exhibiting improved traits, wherein applying the method of this invention.

EXAMPLES

The following examples illustrate certain embodiments of the invention but are not meant to limit the scope of the claims in any way. The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, percentages are weight per weight, molecular weight is weight average molecular weight, temperature is in degrees Centigrade, and pressure is at or near atmospheric.

Reference is made to the following non limiting examples:

Example 1: Experimental Protocol for Soybean Conditioning

Commercial soybean seeds were planted in individual pots in greenhouse equipped with different light sources at different wavelengths. Red light was applied by lamp at about 660 nm. Red and white light were applied by a lamp such as Osram Lumilux L 36/60 or L. 18W/60. Light radiation was applied for a period of between 5 minutes to 2.5 hours, in the presence of ambient daylight characterized by luminous flux units of between about 1.5 to about 3000 lux, particularly between about 100 to about 2000 lux, more particularly in the range of about 800 to about 1800 lux. In this embodiment the light radiation treatment was applied about one hour at dawn or during sunset (dependent on day length), i.e. in the presence of about 1650 lux, every day for the duration of one month from sowing of the seeds into pots. Different combinations of light radiation were applied, in accordance with the genomic structure and expression of each crop. All seedlings were monitored each day and growth measurements were taken and recorded. In addition, nitrogen concentration in the leaves was calculated, e.g. by imaging analysis. It is herein submitted that in certain aspects, the nitrogen concentration measurement is used as an indicator for protein production and protein level in the leaves. Controlled plants did not receive additional light radiation treatment over ambient sunlight. Each treatment or control group contained at least 10 plants.

After one month of treatment, plants which demonstrated improved growth capabilities and higher nitrogen concentration were selected for field growth. Plants were monitored during their life cycle, for example by in vivo measurements of their photosynthesis activities. It is emphasized that the measurements made during the plant life cycle, did not interfere with the plant physiology and did not harm the leaf. At harvesting time, each plant was collected and photographed. The pods and seeds were counted and weighted. The treatment protocol as described above may be repeated for at least four generations.

Example 2: Effect of Treatment Protocol on Treated Soybean Plants as Compared to Untreated Control Plants Reference is now made to FIG. 3, photographically presenting F1 (first generation) of treated versus non treated commercial soybean plants at the age of 10 weeks. This figure clearly shows that the treated plants grow significantly faster than the controlled plants.

The difference in pods numbers of several soybean lines is demonstrated in FIG. 4. It is herein acknowledged that pods numbers are used as estimation methods by farmers for evaluation of future yield in a field during growth period. In this embodiment, the treated F1 lines (first generation) received one treatment, while F2 plants (second generation) received two treatments. As shown in FIG. 4, treated F2 soybean plants exhibited significantly higher pods numbers (up to about 7-fold increase) as compared to the pods numbers of F1 treated and control plants.

The results presented above were further validated by evaluation of average seed number and seed weight, demonstrated in FIGS. 5 and 6 respectively. In those figures, the F2 soybean plants exposed to two treatments, exhibited a dramatic yield increase of up to 3 fold in average seeds number, and between 2.5 and 6.5-fold raise in average seed weight, as compared to the F1 plants exposed to one treatment.

Thus FIG. 5 and FIG. 6 present difference in soybean seeds number and average seeds weight, respectively, between treated and non-treated plants at F1 and F2 generations. In both figures, F2 treated soybean plants showed a dramatic increase in the tested yield parameter, i.e. seeds number and average seeds weight as compared to control and treated F1 plants.

In summary, the results described above demonstrate that the treatment method of the present invention provides F2 soybean plants with significantly increased desirable yield parameters, including pods number, seeds number and average seed weight.

At F3 generation (third generation), which received 3 treatments, additional profound changes were observed in several aspects of the soybean physiology. For example:

1. Average soybean stems width: the main stem width of control F1 plants is about 0.5 cm (African Journal of Biotechnology Vol. 10 (65), pp. 14392-14398, 24 Oct. 2011 and FIG. 7), while the main stem width of the treated selected F3 plants is more than 3 cm
2. An increase in biomass and number of stems was observed in the treated F3 soybean plants as compared to F1 control plants.

It is herein noted that the changes observed are repeated or maintained in F3 without any additional treatment.

The stability of the desirable high yield epigenetic effects was demonstrated. In this experiment, a comparison between the average seeds weight of F2 and F3 control (which is an F3 without any additional treatment) plants of the same line, both received two treatments, was made. Each group contained 10 plants. As shown in FIG. 6, in almost all F3 control sub-lines, sowing without any additional treatment resulted in elevated average seed weight relative to F2 plants of the same line (2 generations, 2 consecutive treatments). The treated soybean plants preserve high yield crop level achieved in previous generation without any additional treatment. It is shown that the treated lines increase their high yield potential in F3 control compared to F2 plants of the same line, without any additional treatment.

Example 3: Effect of Applying Different Treatment Protocols on Yield Parameters of Treated Soybean Plants as Compared to Untreated Control Plants It is herein submitted that different treatment protocols i.e. light regimes, have different effects on yield of soybean plants. In one protocol, the plants were irradiated for one month from the time of sowing, with red light at the wavelength of about 660 nm for one hour at dawn (protocol B). This treatment protocol is shown to result in a dramatic increase in crop yield by about 80% and more than 500% between F2 and F3 (receiving 3 treatments) generations. On the other hand, irradiation with white light (protocol A) resulted in decreased effects on crop yield. Thus it can be concluded that different sub-lines response in different magnitudes to the treatment protocols.

The effect of different treatment protocols on crop yield: The results presented in this figure represent an average of at least 10 plants per group. It is shown that Protocol A decreased the effect while Protocol B increased the high yield effect on soybean plants of the lines tested. In this experiment, both F2 generation plants (which have received 2 treatments) as well as F3 generation plants (also received 2 treatments) served as control populations for the F3 generation plants additionally exposed to Protocol A (Pro A) or Protocol B (ProB) treatments. As shown in FIG. 9, different sub-lines response at different magnitude to the treatment protocols. For example, in 162 sub-line, it was observed that the F3 control plants exhibited increased seed weight relative to the F2 plants. The F3 plants treated with Protocol A exhibited decreased seed weight while F3 plants treated with Protocol B exhibited increased seed weight, as compared to F2 and F3 controls. The same mode of behavior or effect can be seen in the other tested sub-lines but in different magnitudes, e.g., the C62 sub-line exhibits more than two-fold average seed weight increase (more than 100% average seed weight increase) as a result of exposure to Protocol B treatment.

Reference is now made to Table 2, summarizing the results of F3 experiments with different soybean sub-lines. All numbers in the table represent average of at least 10 plants per group. The USA average numbers (**), taken for comparison, are obtained from the University of Kentucky.

TABLE 2

Summary of the F3 soybean experiments results

| Line number | Type | No. of pods in F3/plant | Weight of pods in F3 (gr/plant) | Average number of seeds in F3/plant | Weight of seeds in F3 (gr/plant) | Average seed weight per plant (gr) | Increase seeds weight in F3 ProB versus F3 Con |
|---|---|---|---|---|---|---|---|
| H100 F3 ProB | Oil | 97.4 | 51.15 | 260.6 | 33.23 | 0.116 | +97.5% |
| L100 F3 ProB | Oil | 102 | 61.56 | 281.3 | 37.23 | 0.132 | +161.4% |
| P100 F3 ProB | Oil | 85.89 | 37.02 | 231.4 | 24.99 | 0.108 | −0.6% |
| C62a F3 ProB | Oil | 70.67 | 14.96 | 160.44 | 17.12 | 0.107 | +81.82% |
| C62b F3 ProB | Oil | 76.3 | 38.15 | 193.6 | 21.89 | 0.113 | +237.7% |
| I62 F3 ProB | Oil | 56 | 26.35 | 137.1 | 15.31 | 0.112 | +134.5% |
| E2 F3 ProB | Tofu | 100 | 62.31 | 252.9 | 36.45 | 0.144 | +332.8% |
| B2 F3 ProB | Tofu | 28.27 | 35.32 | 158 | 20.77 | 0.131 | +328.1% |
| I88 F3 ProB | Tofu | 135 | 87 | 333.5 | 69.49 | 0.208 | +395.6% |
| K88 F3 ProB | Tofu | 122.8 | 97.81 | 353.4 | 62.43 | 0.177 | +172.8% |
| L88 F3 ProB | Tofu | 163.8 | 121.1 | 427.6 | 84.21 | 0.196 | +507.3% |
| USA average numbers** | | 20-30 | | 62.5 | 9.4 | 0.15 | |

The results of Table 2 are further summarized in a graphic illustration presented in FIGS. 12-13. The results represent the average yield of at least 10 plants per group.

From the results presented in Table 2 and FIGS. 12-13, it can be seen that some sub-lines did not reach their full high yield potential even after 3 generations (3 treatments), while the other did. This effect can be observed by comparing the yield between F3 control (which received two treatments) and F3 with additional treatment, receiving altogether 3 treatments. More particularly, lines H100, P100, C62a and I62 probably have reached full yield potential since there is no statistical difference between the control group and the treated groups. Other lines probably have not reached the full yield potential since the treated groups show statistically higher yield than the control groups.

Example 4: Photosynthesis Monitoring in Treated Sub-Lines Versus Control

Reference is now made to the PTM Photosynthesis Monitor principle of operation. In one embodiment, the photosynthesis monitoring was performed by the PTM-48M device. The PTM-48M Photosynthesis Monitor is a four-channel automated system for monitoring $CO_2$ exchange and transpiration of leaves. The system is equipped with a set of four original self-clamping leaf chambers, which operate one-by-one in such a manner that one of leaf chambers is closed at a time while the others remain open.

The automatic self-clamping design enables keeping a leaf open for more than 90% of the time. Thus, the leaf environment is not disrupted considerably.

In the open photosynthesis system, the $CO_2$ exchange is determined on the basis of the depression of $CO_2$ concentration at the outlet ($C_{out}$) of the leaf chamber in comparison with the incoming ambient air ($C_{in}$). The $CO_2$ exchange rate is calculated as follows:

$$E = k \times (C_{in} - C_{out}) \times F,$$

where F is the air flow rate and k is a dimension factor, which depends on air temperature and pressure and is calculated by the system automatically.

Transpiration rate is determined by the following equation:

$$Tr = (H_{out} - H_{in}) \times F;$$

where H is the absolute concentration of water vapor in the air. To shorten the measurement cycle, the $H_{out}$ is computed during a transient period between $20^{th}$ and $30^{th}$ second after closing the chamber. The calculation algorithm also takes into account the rising humidity inside the chamber and, hence, allows determining the initial transpiration rate at the ambient air humidity. The cycle starts from the purging the system that continuous 120 seconds. All chambers are open and purged at this stage. Then, during the reference stage, only the chamber No. 1 is connected to the measuring system. This stage continues until the steady-state concentration has been reached. In any case the reference stage stops after 60 seconds and the chamber No. 1 closes. At the end of 30-second measurement stage the records for Chamber #1 are ready. Then, the second chamber repeats both reference and measurement cycles. If optional sensors are connected to the system, their readings are collected during operation of all leaf chambers. At the end of the measurement cycle, the average values are recorded.

The typical duration of the operational cycle with 4 leaf chambers is about 6 minutes while each chamber is closed only 30 seconds. Typical (recommended) the time interval between cycles is 30 minutes.

Selected plants were followed for several life cycles to monitor their growth capacity and other characteristics which are related directly to the predetermined treatment. One of the major aims of this procedure was to evaluate the stability of the genome of the selected plants and to evaluate the plant ability to conserve its increased growth potential for several generations.

Reference is now made to FIG. 17 graphically presenting a comparison of photosynthesis level between treated and control Bantam line corn plants of F3 ($3^{rd}$ generation) sub-line L-100. The measurements were taken every 5 minutes between 8:24 AM to 14:24 PM. Each point in the graph represents an average of two measurements. As shown in this figure, there is a difference of up to 150% (about 2.5 fold) between the treated plants versus the control plants.

Example 5: High Yield Tomato Experiment

Reference is now made to treatment protocols applied to tomato plants. In a specific embodiment, tomato commercial seeds were used (i.e. variant line number 189 of Hazera, Israel). The seeds were divided into two groups; one served as control and the other received treatment protocol as disclosed inter alia (protocol B) for one month from sowing. Each group contained about 150 seeds. The seeds were sown in pots and kept in greenhouses. After about one month, the highest performing yield plants were transferred to field growth conditions. In this experiment, about 25 plants from the control greenhouse and 23 from the treated greenhouse plants were transferred to field growth conditions. The harvesting time was between August and September growing seasons. The total number of fruits and their weight were evaluated for each plant, and average fruit number and fruit weight values were calculated. Seeds from the best performing plants were collected.

TABLE 3

Summary of F1 results of treated (one treatment) versus control (no treatment) Tomato plants

| plant number | Number of tomatoes/plant | Weight of tomatoes kg/plant |
| --- | --- | --- |
| 1 | 28 | 3.07 |
| 3 | 27 | 3.18 |
| 5 | 21 | 3.02 |
| 6 | 32 | 2.63 |
| 7 | 33 | 2.57 |
| 9 | 36 | 2.09 |
| 15 | 27 | 3.10 |
| 16 | 29 | 1.9 |
| 18 | 29 | 2.3 |
| 19 | 30 | 2.8 |
| 22 | 33 | 2.6 |
| 26 | 27 | 1.8 |
| 27 | 29 | 1.9 |
| 28 | 29 | 2.5 |
| 29 | 28 | 2.9 |
| 30 | 31 | 3.1 |
| 31 | 33 | 2.4 |
| 33 | 36 | 2.7 |
| 34 | 29 | 3.0 |
| 36 | 26 | 3.1 |
| 37 | 29 | 2.8 |
| 38 | 30 | 2.3 |
| 39 | 31 | 2.1 |
| 41 | 30 | 2.4 |
| 42 | 33 | 2.8 |
| Average | 29.84 ± 3.236 | 2.6 ± 0.421 |
| Treatment group (protocol B) | | |
| 7 | 37 | 3.7 |
| 15 | 41 | 3.3 |
| 26 | 39 | 3.8 |
| 33 | 51 | 4.6 |
| 35 | 49 | 3.9 |
| 39 | 61 | 4.2 |
| 45 | 39 | 3.9 |
| 49 | 41 | 3.7 |
| 51 | 51 | 4.5 |
| 53 | 55 | 5.5 |
| 56 | 58 | 4.6 |
| 59 | 32 | 3.2 |
| 64 | 29 | 2.8 |
| 74 | 38 | 3.9 |
| 76 | 43 | 4.2 |
| 78 | 49 | 4.5 |
| 83 | 22 | 2.2 |
| 86 | 46 | 4.0 |

TABLE 3-continued

Summary of F1 results of treated (one treatment) versus control (no treatment) Tomato plants

| | Number of tomatoes/plant | Weight of tomatoes kg/plant |
|---|---|---|
| 89 | 41 | 4.0 |
| 92 | 39 | 3.4 |
| 105 | 40 | 3.8 |
| 109 | 45 | 4.5 |
| 113 | 49 | 4.5 |
| Average | 43.26 ± 9.116 | 3.9 ± 0.688 |

The results presented in Table 3 show that, F1 tomato plants treated with the treatment regime of the present invention (i.e. protocol B) exhibited increased tomato yield. Particularly, an increase of about 185% in fruits number and of about 156% in fruit weight was observed in the treated tomato plants relative to the control plants.

Example 6: High Yield Stevia Experiment

Reference is now made to the high yield stevia experiment. Stevia is a plant that is native to South America and it is known as a source of natural sweeteners. In fact, native people in South America have used stevia as a sweetener for hundreds of years. But the leaves are also used to make medicine.

As shown in FIG. 12, the Tofu soybean plants responded to the conditioning treatment protocol by increasing biomass and by accelerating growth in comparison to control untreated Tofu soybean plants.

Example 7: High Yield Corn Experiment

Two commercial Australian corn lines were used in the F1 experiment, namely Bantam and True gold. These corn lines were exposed to various treatment protocols (i.e. treatment protocols A and B or a combination thereof). When Protocol B was applied, a sharp increase of about 146% was observed in seed weight, in the True gold line. Table 4 summarizes the results of the F1 corn experiment.

TABLE 4

High yield F1 Corn experimental results

| Line name/type of treatment | Number of plants per group | Average number of seeds | Increase in treated seed number over control seed number in % | Average seeds weight in gr. | Increase in treated seed weight over control seed weight in % |
|---|---|---|---|---|---|
| Bantam/control | 12 | 267.3 | | 58.7 | |
| Bantam/treatment | 12 | 362.5 | 35.6% | 79.2 | 34.9% |
| True gold/control | 24 | 313.5 | | 53.1 | |
| True gold/treatment | 19 | 509.7 | 62.6% | 130.8 | 146.3% |

As shown in Table 4, an increase of between about 30% and about 65% was observed in the seed number of treated plants as compared to control corn plants. In addition, the treated corn plants exhibited an increase of between about 30% and about 150% in seed weight over the control corn plants.

In another embodiment, the average height of 21 days treated corn seedlings was tested. This experiment refers to the following seed generations and treatments definitions:

F0—commercial seeds

F0/2—commercial seeds sowed again at F1 as control and reference for treatment starting point.

F1—F1 exposed to one treatment

F1/2—F2 sowing without any additional treatment, served as control for F2 which received 2 treatments.

F2—F2 exposed to two treatments

TABLE 5

Corn average height results

| Plant line | Generation | Height in cm. |
|---|---|---|
| True gold | F0/2 | 39.4 |
| True gold | F1/2 | 69.9 |
| True gold | F2 | 78.4 |
| Bantam | F0/2 | 42.3 |
| Bantam | F1/2 | 53.9 |
| Bantam | F2 | 63.27 |

It is shown in Table 5 that plant height of corn seedlings was increased by up to two fold (particularly between 40% and 100%) at F2 seedlings exposed to two treatments as compared to the reference untreated seedlings.

Example 8: Experimental Protocol for Corn Conditioning

An exemplified treatment applied to the seeds or seedlings include the following experimental protocol: The commercial corn seeds were planted in individual pots in greenhouse equipped with different light sources at different wavelengths. Red light was applied by lamp at about 660 nm. Red and white light were applied by a lamp such as Osram Lumilux L 36/60 or L. 18W/60. Light radiation was applied for a period of between 5 minutes to 2.5 hours, in the presence of ambient daylight characterized by luminous flux units of between about 1.5 to about 3000 lux, particularly between about 100 to about 2000 lux, more particularly in the range of about 800 to about 1800 lux. In this embodiment the light radiation treatment was applied about one hour at dawn or during sunset (dependent on day length), i.e. in the presence of about 1650 lux, every day for the duration of one month from sowing of the seeds into pots. Different combinations of light radiation were applied, in accordance with the genomic structure and expression of each crop. All seedlings were monitored each day and growth measurements were taken and recorded. Control plants did not receive additional light radiation treatment over ambient sunlight. Each treatment or control group contained at least 10 plants.

After about one month of treatment, plants which demonstrated improved growth capabilities were selected for field growth. Plants were monitored during their life cycle, for example by in vivo measurements of their photosynthesis activities. It is emphasized that the measurements made during the plant life cycle, did not interfere with the plant physiology and did not harm the leaf. At harvesting time, each plant was collected and photographed. The seeds of each plant were counted and weighted. The treatment protocol as herein described may be repeated for at least two generations and up to four generations and more.

Example 9: Effect of the Treatment Protocol of the Present Invention on Yield Parameters of Treated Corn Plants as Compared to Untreated Control Plants Experimental Procedure In this experiment, two commercial Australian lines were used as examples of seeds that may be treated with the protocol of the present invention: 'Golden Bantam' also called 'Bantam' and 'True Gold' (http://sustainableseedco.com/heirloom-vegetable-seeds/ce-k/corn-heirloomseeds/heirloom-sweet-corn-seed/original-8-row-golden-bantam corn.html.http://www.smartgardener.com/plants/218-corn-true-gold/overview).

'Bantam' is a tender annual, non-hybrid commercial line, producing sweet corn. 'True Gold' is a tender annual open pollinated corn.

The following procedure was applied to the commercial seeds:
1. Each seed was planted in an individual pot, germinated and grew for one month in greenhouse.
2. During this month the seeds and seedlings received their designated treatment, or no treatment, in case of control. All plants received the same agronomic conditions during their growth cycle (both treated and control plants).
3. One month old best performing seedlings were selected and transferred to field growth conditions.
4. Daily 10 minutes drip irrigation was applied to the field grown seedlings, all together about 400 mm/season.

Reference is now made to FIG. 19 illustrating a flow chart describing the various seed generations and treatments applied to the seeds and seedlings in each generation, as an embodiment of the present invention. In this chart, F0; F1; F2 and F3 refer to the seed generations and Tr.1; Tr.2 and Tr.3 refer to the number of treatments applied to the seeds and seedlings. In this embodiment, treated F1 seeds received one treatment (Tr. 1), F2 seeds received two treatments (one in F1 and one in F2) (Tr. 2) and F3 seeds received three treatments, one in each generation (Tr. 3). The F0, Tr.0 seeds are the initial commercial seeds with no treatment.

It is further noted that each treatment in the trial is equivalent and equal. That is to say that where, in the chart, 2 treatments are designated, the seeds have received 2×1 treatment, or, where 3 treatments are designated the seeds have received 3×1 treatment. The treatments were administered vertically down the generations, and no generation received more than 1 treatment in that generation. As can be seen in FIG. 1, in each generation, comparisons were made between untreated seeds and seeds that received one or more treatments.

It should be noted that the second treatment plants marked with a '*' grew off-season in the south of Israel. The second treatment plants (Tr.2) marked with '' grew in-season at Epigenetics location. The boxes marked with '*' refer to plants planted and harvested in the center of Israel.

The treated and non-treated/control seeds were planted in April and harvested in August. The seeds and/or seedlings were treated in greenhouses and then transferred to field growth conditions. Seeds from selected high yield plants from the previous generation were treated with the technology and protocol of the present invention, in the subsequent growing season, and compared to untreated seeds of the same generation planted at the same time.

A field trial has been performed comparing seeds that received one treatment (Tr.1), two treatments (Tr.2), three treatments (Tr.3) with untreated F3 seeds (F3, Tr.0). At least 10 selected plants (up to 25 plants in some experimental groups) were transferred from greenhouse to the field. At this stage, continuous measurements of in-vivo photosynthetic rate were taken over 24 to 48 hours during the plant's vegetative phase. At harvest time, seeds from each plant were collected, dried, counted and weighed. Average and standard deviation values were calculated.

Experimental Results

Reference is now made to FIG. 22 presenting evaluation of the effect of the treatment protocol of the present invention on the average seed number per plant of treated versus non treated 'Bantam' corn line. The increased average seed number per plant has been observed in F3 'Bantam' corn seeds exposed to one treatment (F3, Tr. 1) and in F2 'Bantam' corn seeds exposed to two treatments (F2, Tr. 2) relative to non-treated F3 seeds (F3, Tr. 0). Interestingly, the average number of seeds per plant has been dramatically increased, i.e. by about 1.8 fold (FIG. 24) or by about 80% (FIG. 25), in F3 'Bantam' corn seeds exposed to three treatments (F3, Tr. 3) relative to the non-treated control F3 seeds (F3, Tr. 0).

A similar trend has been observed when evaluating the effect of the treatment protocol of the present invention on the average seed number per plant of treated versus non treated 'True Gold' corn line (see FIG. 23). As shown, an increased average seed number per plant has been observed in F3 'True Gold' corn seeds exposed to one treatment (F3, Tr. 1) and in F2 'True Gold' corn seeds exposed to two treatments (F2, Tr. 2) relative to non-treated F3 seeds (F3, Tr. 0). A dramatic increase i.e. of about 1.8 fold (FIG. 3A) or of about 70% (FIG. 3B) has been observed in average number of seeds per plant of F3 'True Gold' corn seeds exposed to three treatments (F3, Tr. 3) relative to the non-treated control F3 seeds (F3, Tr. 0).

These experimental results clearly demonstrate that by treating corn seeds and/or seedlings by the unique protocol of the present invention, significantly high yield corn plants are produced. The effect is maintained down the generations (e.g. F3 Tr. 1), and is increased by repeating the treatments (e.g. F2, Tr.2 and F3, Tr. 3).

Reference is now made to FIG. 12, graphically presenting evaluation of average seed weight per plant of treated versus non treated 'Bantam' lines. This experiment summarizes the results of high yield sub-lines exposed to the treatment protocol of the present invention (Tr. 1, Tr. 2 and Tr. 3) as compared to control non treated (Tr. 0) F3 seeds. It is demonstrated that the average seed weight per plant is gradually increasing in correlation with the number of treatments applied to the seeds. The average seed weight per plant of treated F3 plants (Tr. 3) is shown to be significantly higher than untreated F3 control seeds, i.e. about 1.8 fold higher or by 80% higher as compared to F3 untreated seeds (F3, Tr. 0).

With respect to 'True Gold' line seeds, it is surprisingly demonstrated in FIG. 13 that while no effect was observed as a result of the second treatment (F2, Tr. 2) over the first treatment (F3, Tr. 1), the average seed weight per plant was dramatically increased by about 2 fold (FIG. 5A) in F3 seeds exposed to three treatments (F3, Tr. 3) as compared to none treated F3 seeds (F3, Tr. 0).

The results described above show that the treatment protocols provided by the present invention produce advantageous corn plants with desired elevated yield parameters of increased average number of seeds per plant and increased average seeds weight per plant.

Reference is now made to FIG. 14 graphically presenting evaluation of average weight of a single seed of treated 'Bantam' line seeds versus untreated F3 seeds. In this experiment, each bar represents an average of 200 seeds. It is shown in this Fig. that in the F3 Tr. 3 seeds, the average weight of a single seed was increased by about 1.3 fold (FIG. 14) relative to untreated F3 (Tr. 0) seeds. Similar results have been obtained with the 'True Gold" line seeds (see FIG. 15).

Reference is now made to Table 1, summarizing the corn yield results described in this example.

TABLE 6

Summary of corn yield results

| Seed Line | Generation F3, Tr.3 versus F3, Tr.0 | Increased Seed number in % | Increased weight of a single seed in % | Increased total seed weight in % |
|---|---|---|---|---|
| Bantam | Tr.0 versus Tr.3 | Seed number 83% $P < 0.001$ | Single seed weight 34.6% $P = 0.2514$ | Total seed weight 86.3% $P < 0.001$ |
| True Gold | Tr.0 versus Tr.3 | Seed number 82.3% $P < 0.001$ | Single seed weight 22.3% $P < 0.001$ | Total seed weight 120.5% $P < 0.001$ |

It is noted that a p-value 2-tailed t-test was performed between the non-treated F3, Tr.0 plants versus F3, Tr.3 treated plants.

It is further noted that the F2 seeds for this experiment were grown in the south of Israel during the winter ("off season" seeds). It is herein acknowledged that off-season seeds maybe inferior in quality as compared to "in-season" seeds. Therefore, better yield results may have been observed in the treated F3 plants if F2 seeds generated from plants grown "in-season" had been available for the subsequent treatment and planting.

In summary, the results described above demonstrate that the treatment method of the present invention provides F2 and F3 corn plants with significantly increased desirable yield parameters, including elevated average seed number per plant, elevated average seed weight per plant and elevated average single seed weight.

Example 10: Effect of the Treatment Protocol of the Present Invention on Photosynthetic Rate of Treated Corn Plants as Compared to Untreated Control Plants In this experiment, photosynthetic rate of 'Bantam' (FIG. 17) and 'True Gold' (FIG. 18) exemplary corn lines was evaluated in treated versus control groups. Measurements were taken at 30 minute intervals over a 24 or 48 hours period of time, on 4 leaves from 4 plants (two from each group) at the same time of day. The continuous and simultaneous measurements ensure an accurate monitoring of the photosynthetic rate for the two (treated and control) plant groups under evaluation. It is noted that the photosynthetic rate was calculated according to the following data evaluated in each measurement: ambient $CO_2$; $CO_2$ exchange (absorbed $CO_2$); air flow; absolute humidity; transpiration; radiation; air temperature; leaf temperature; vapors pressure; atmospheric pressure and dew point.

The measurements were taken, preferably using the PTM 48A photosynthesis and transpiration monitor at the vegetative stage of the plant. Automatic self-clumping leaf cells, i.e. a self-clamping leaf chambers LC-4A (Ben-Asher J. et al. Effect of temperature on photosynthesis and transpiration of corn in a growth chamber. The annual meeting of the Amer. Soc. Agron. New Orleans, November 2007. P. 321-2, is herein incorporated by reference) was used.

The measured average photosynthetic rate of the treated plants (F3, Tr.3) is significantly higher than the measured average photosynthetic rate of the control plants (F3, Tr.0) throughout most of the evaluation period. Moreover, the peak photosynthetic rate value of treated F3 'Bantam' line (Tr.3) is about 80% higher than untreated F3 (Tr.0) at the same time point.

The photosynthetic rate measuring results as described inter alia demonstrate that a higher photosynthetic rate is measured in treated corn plants versus non treated plants of the same corn line. This means that as a result of the treatment protocol of the present invention increased energy is supplied to the plant enabling it to produce an increased yield.

Example 11: Experimental Protocol for Corn Conditioning

The exemplified treatment applied to the seeds or seedlings is as described in Example 1.

Example 12: Effect of the Treatment Protocol of the Present Invention on Yield Parameters of Treated Corn Plants as Compared to Untreated Control Plants Experimental Procedure In this experiment, one commercial Australian line was used as example of seeds that may be treated with the protocol of the present invention, i.e. 'Golden Bantam' also called 'Bantam' (http://sustainableseedco.com/heirloom-vegetable-seeds/ce-k/corn-heirloom seeds/heirloom-sweet-corn-seed/original-8-row-golden-bantam corn.html).

'Bantam' is a tender annual, non-hybrid commercial line, producing sweet corn.

The following procedure was applied to the commercial seeds:
1. Each seed was planted in an individual pot, germinated and grew for one month in greenhouse.
2. During this month the seeds and seedlings received their designated treatment, or no treatment, in case of control. All plants received similar agronomic conditions during their growth cycle (both treated and control plants).
3. One month old best performing seedlings were selected and transferred to field growth conditions.
4. Daily 10 minutes drip irrigation was applied to the field grown seedlings, all together about 400 mm/season.

Reference is now made to FIG. 19 illustrating a flow chart describing the various seed generations and treatments applied to the seeds and seedlings in each generation, as an embodiment of the present invention. In this chart, F0; F1; F2 and F3 refer to the seed generations and Tr.1; Tr.2 and Tr.3 refer to the number of treatments applied to the seeds and seedlings. In this embodiment, treated F1 seeds received one treatment (Tr. 1), F2 seeds received one or two treatments (one in F1 and one or none in F2) (Tr. 2) and F3 seeds received three treatments, one in each generation (Tr. 3). The F0, Tr.0 seeds are the initial commercial seeds with no treatment.

It is further noted that each treatment in the trial is equivalent and equal. That is to say that where, in the chart, 2 treatments are designated, the seeds have received 2×1 treatment, or, where 3 treatments are designated the seeds have received 3× treatment. The treatments were administered vertically down the generations, and no generation received more than one treatment in that generation. As can be seen in FIG. 8, in each generation, comparisons were made between untreated seeds and seeds that received one or more treatments.

The seeds and/or seedlings were treated in greenhouses and then transferred to field growth conditions. Seeds from selected high yield plants from the previous generation were treated with the technology and protocol of the present invention, in the subsequent growing season, and compared to untreated seeds of the same generation planted at the same time.

A field trial has been performed comparing seeds that received one treatment (Tr.1), two treatments (Tr.2), three treatments (Tr.3) with untreated F3 seeds (F3, Tr.0). At least 10 selected plants (up to 25 plants in some experimental groups) were transferred from greenhouse to the field. At harvest time, seeds from each plant were collected, dried, counted and weighed. Average and standard deviation values were calculated.

Experimental Results

Reference is now made to FIG. 22 presenting evaluation of the effect of the treatment protocol of the present invention on the average seed number per plant of treated versus non treated 'Bantam' corn line. As can be seen in FIG. 22, an increased average seed number per plant has been observed in F3 'Bantam' corn seeds exposed to two treatments (F3, Tr. 2) and in F3 'Bantam' corn seeds exposed to three treatments (F3, Tr. 3) relative to non-treated F3 seeds (F3, Tr. 0). Interestingly, the average number of seeds per plant has been dramatically increased, i.e. by about 1.3 fold (F3, Tr. 2) or by about 1.4 fold (F3, Tr. 3), relative to the non-treated control F3 seeds (F3, Tr. 0).

These experimental results reinforce the results described in example 1, that by treating corn seeds and/or seedlings by the unique protocol of the present invention, significantly high yield corn plants are produced. The effect is maintained down the generations (e.g. F3 Tr. 1), and is increased by repeating the treatments (e.g. F2, Tr.2 and F3, Tr. 3). It has been shown for both tested corn lines that plants which received 2 treatments maintained their effect for at least one generation without receiving an additional treatment.

The average seed weight per plant of treated versus non treated 'Bantam' lines: This experiment summarizes the results of high yield sub-lines exposed to the treatment protocol of the present invention (Tr. 1, Tr. 2 and Tr. 3) as compared to control non treated (Tr. 0) F3 seeds. It is demonstrated that the average seed weight per plant is gradually increasing in correlation with the number of treatments applied to the seeds. The average seed weight per plant of treated F3 plants (Tr. 3) is shown to be significantly higher than untreated F3 control seeds, i.e. about 1.4 fold higher (FIG. 13A) or by 33% higher (FIG. 13B) as compared to F3 untreated seeds (F3, Tr. 0).

The results described above show that the treatment protocols provided by the present invention produce advantageous corn plants with desired elevated yield parameters of increased average number of seeds per plant and increased average seeds weight per plant.

The average weight of a single seed of treated 'Bantam' line seeds versus untreated F3 seeds: In this experiment, each bar represents an average of 200 seeds. It is shown in this Fig. that in the F3 Tr. 3 seeds, the average weight of a single seed was increased by about 1.3-fold relative to untreated F3 (Tr. 0) seeds.

Reference is now made to Table 2, summarizing the corn yield results described in this example.

TABLE 7

Summary of corn yield results

| Seed Line | Generation F3, Tr.3 versus F3, Tr.0 | Increased seed number in % | Increased weight of a single seed in % | Increased total seed weight in % |
|---|---|---|---|---|
| Bantam | Tr.0 versus Tr.3 | Seed number 38% P = 0.04605 for 1 tail | Single seed weight 21% P < 0.001 | Total seed weight 33% P = 0.0018, 2 tails |

It is noted that a p-value 2-tailed t-test was performed between the non-treated F3, Tr.0 plants versus F3, Tr.3 treated plants, unless otherwise mentioned.

In summary, the results described above demonstrate that the treatment method of the present invention provides F2 and F3 corn plants with significantly increased desirable yield parameters, including elevated average seed number per plant, elevated average seed weight per plant and elevated average single seed weight.

Example 13: Effect of the Treatment Protocol of the Present Invention on Phenotypic Characteristics of Treated Corn Plants as Compared to Untreated Control Plants In this experiment, phenotypic characteristics of 'Bantam' exemplary corn line was evaluated in treated versus control groups. Evaluation was performed visually. The most relevant differences are summarized as follows:

Multiple (more than 2) ears can be seen in the plants. In some of the plants up to 6 ears on a plant were observed, about half of the ears were empty. In other plants, 3, 4 and 5 ears were observed. Less than half ears were empty in these plants. Multiple ears were observed only after 3 rounds of treatments. The majority of the plants presented 2 ears per plant. The size of an average seed of treated F3 plant (Tr.3) was at least twice relative to the control seed, F3 (Tr. 0). The color of the treated seed was dark yellow, while the color of the control seeds was light yellow.

Reference is now made to FIG. 20, presenting a photographic illustration of the multiple ears (shown with arrows) phenotype in (Tr. 3) F3 'Bantam' line.

Reference is now made to FIG. 21, presenting a photographic illustration of differences between the seeds of treated F3 plant (Tr. 3) and the control F3 (Tr. 0) in 'Bantam' line. The average weight of 1 seed is 0.290 gm in the treated plant while in the Control, the average weight of 1 seed is 0.120 gm. As mentioned before the color of a treated seed is dark yellow while the color of a control seeds is light yellow.

Example 14: Stress Resistance

Treated plants are better than control plants in coping with a-biotic stress, such as the root bound effect and reaction to herbicide application Root Bound Effect:

1. Corn seeds were sown in 12 cm pots and placed in greenhouses. 960 seedlings received the treatment of the invention and 200 seedlings were used as control without any treatment. Seedlings were grown in a greenhouse for 4 weeks. At the end of the 4 weeks treatment, the average height of the treated plants was 35 cm, while the average height of the control plants was 20 cm. When seedlings from both groups transferred to field growth conditions, their roots were heavily bounded around the inner part of the pot. The plants demonstrated strong stress effects as light green color of the leaves and poor vigor of the plants. After a few days in the field the treated plants regain their full vigor, while the control plants needed about 2 weeks for regaining their full vigor. Leaves' dark green color in the treated plant reached their peak within one week while it took 3 weeks in the treated plants. The recuperation from root bound stress effects is significantly shorter in the treated plants, while the control plants needed much more time to overcome such stress effect.

Example 15: Herbicide Resistance

Corn seeds were sown directly in the field as field trial conducted by the CRO. Four weeks after sowing, the corn field was spread against weed by the herbicide Laudis 225 as weed control. Eight days after applying the herbicide, phytotoxic effect was observed as white spots appeared on the leaves of both treated and control plants and the vigor of all plants was affected. Three days after applying the herbicide, the treated plants were fully recuperated, while it took about 2 weeks for the control plants to reach full recuperation.

The recovery period from the effect of herbicide is significantly shorter in the treated plants in comparison to the untreated control plants.

The invention claimed is:

1. A method for producing a plant exhibiting improved traits compared to a control population of plants of the same plant species comprising the steps of:
    (a) providing a population of plants;
    (b) exposing said population of plants to a predetermined light treatment regime by irradiating with artificial light in the presence of ambient daylight, characterized by luminous flux units of between about 1.5 to about 3000 lux, from about 100 to about 2000 lux, every day for a duration of up to about 6 weeks from sowing, wherein the predetermined light treatment regime of step (b) comprises:
    irradiating said plants with artificial light of wavelength in the range of from about 600 nm to about 700 nm for a period of from about 30 minutes, to about 60 minutes, starting about 30 min. before sunset or sunrise, and optionally continuing about 30 minutes after sunset or sunrise,
    followed by the following steps:
    (c) monitoring at least one trait of said plants of step (b) and comparing to said control population;
    (d) selecting the top at least about 0.5%, or 1-2% plants having the best improved trait of said plants of step (c);
    (e) propagating at least one subsequent generation of said at least 0.5%, or 1-2% best improved trait plants; and
    (f) optionally repeating steps (b) to (e) on said at least one subsequent generation;
    thereby obtaining a modified plant or part thereof exhibiting improved traits, wherein said improved traits are inheritable for either at least one more generation, for two or more generations, for 3 to 5 generations, or for 6 to 8 generations,
    wherein the improved inheritable traits are selected from the group consisting of increase in yield, increase in pod number, increase in fruit number, increase in seed number, increase in seed weight, increase in main stem width, increase in pod weight, increase in fruit weight, increase in plant biomass, increase in number of stems, increase in photosynthesis efficiency, and any combination thereof, compared to said control population.

2. The method of claim 1, wherein the improved inheritable trait being monitored is inheritable improved yield.

3. The method of claim 1, wherein the modified plant or part thereof is selected from the group consisting of Maize, Rapeseed, Cotton, Corn, Wheat, Rice, Potato, Cassava, Pepper, Tomato, Stevia and any combination thereof, further exhibiting said improved inheritable trait of at least 2% and up to about 200%, or further exhibiting said improved inheritable trait of at least 2%, 5%, 10%, 20%, 30%, 40%, 50%, 60%, 70%, 80%, 90%, 100%, or 200%, as compared to the control population.

4. The method of claim 1, wherein the modified plant or part thereof exhibiting improved inheritable traits is selected from the group consisting of seeds, seedlings, potted seedlings, adult plants and any combination thereof.

5. The method of claim 1, wherein the population of plant is Soybean, Corn, Tomato or Stevia plants.

6. The method of claim 1 wherein said plant is a genetically modified (GM) plant or a non-GM plant.

* * * * *

UNITED STATES PATENT AND TRADEMARK OFFICE
CERTIFICATE OF CORRECTION

PATENT NO. : 11,464,183 B2
APPLICATION NO. : 15/965060
DATED : October 11, 2022
INVENTOR(S) : Avner Shenfeld It is certified that error appears in the above-identified patent and that said Letters Patent is hereby corrected as shown below:

On the Title Page

Item (56), Column 1, Other Publications, Line 7:
Delete "PCT/IL201 6/" and insert -- PCT/IL2016/ --

Item (56), Column 2, Other Publications, Line 3:
Delete "pratives"," and insert -- practices", --

Item (56), Column 2, Other Publications, Line 3:
Delete "Confererence," and insert -- Conference, --

Item (56), Column 2, Other Publications, Line 21:
Delete "helrloom-" and insert -- heirloom- --

Item (56), Column 2, Other Publications, Line 22:
Delete "heirioom-" and insert -- heirloom- --

Item (56), Column 2, Other Publications, Line 22:
Delete "-cor-" and insert -- -corn- --

Item (56), Column 2, Other Publications, Line 27:
Delete "Yugosa")," and insert -- Rugosa)", --

Item (57), Column 2, Abstract, Line 13:
After "for" insert -- at --

Signed and Sealed this
Twentieth Day of December, 2022

Katherine Kelly Vidal
*Director of the United States Patent and Trademark Office*